(12) United States Patent
Shah

(10) Patent No.: US 6,916,621 B2
(45) Date of Patent: Jul. 12, 2005

(54) METHODS FOR ARRAY-BASED COMPARITIVE BINDING ASSAYS

(75) Inventor: Shishir Shah, Houston, TX (US)

(73) Assignee: Spectral Genomics, Inc., Houston, TX (US)

( * ) Notice: Subject to any disclaimer, the term of this patent is extended or adjusted under 35 U.S.C. 154(b) by 75 days.

(21) Appl. No.: 10/112,657

(22) Filed: Mar. 27, 2002

(65) Prior Publication Data

US 2003/0186250 A1 Oct. 2, 2003

(51) Int. Cl.[7] .................... C12Q 1/68; C12N 11/16; C12M 1/00; C07H 21/04
(52) U.S. Cl. .................... 435/6; 435/7.1; 435/174; 435/283.1; 435/287.2; 536/23.1; 536/24.3
(58) Field of Search .................... 435/6, 7.1, 174, 435/283.1, 287.2; 536/23.1, 24.3

(56) References Cited

U.S. PATENT DOCUMENTS

| | | | |
|---|---|---|---|
| 5,760,130 A | 6/1998 | Johnston et al. | 525/54.2 |
| 5,807,522 A * | 9/1998 | Brown et al. | 422/50 |
| 5,830,645 A * | 11/1998 | Pinkel et al. | 435/6 |
| 5,843,767 A * | 12/1998 | Beattie | 435/287.1 |
| 6,251,601 B1 * | 6/2001 | Bao et al. | 435/6 |
| 6,258,454 B1 | 7/2001 | Lefkowitz et al. | 428/333 |
| 6,335,167 B1 | 1/2002 | Pinkel et al. | 435/6 |
| 6,346,413 B1 | 2/2002 | Fodor et al. | 435/287.2 |
| 2002/0015960 A1 | 2/2002 | Liang et al. | 435/6 |

FOREIGN PATENT DOCUMENTS

WO WO 01/42501 A1 6/2001

OTHER PUBLICATIONS

DeRisi et al "Exploring the metabolic and genetic control of gene expression on a genomic scale" Scinece, 1997, 278: 680–686.*

Marton et al "Drug target validation and identification of secondary drug target effects using DNA microarrays" Nature Medicin 1998, 4: 1293–1301.*

* cited by examiner

Primary Examiner—B J Forman
(74) Attorney, Agent, or Firm—Mintz, Levin, Cohn, Ferris, Glovsky and Popeo, P.C.; Ivor R. Elrifi; Matthew Pavao

(57) ABSTRACT

The invention provides computer systems, computer program products and methods for in silico array-based methods for determining the relative amount of biological molecules (e.g., nucleic acid sequences) in two or more samples. The invention also provides novel arrays comprising immobilized calibration molecules (e.g., nucleic acids) for normalizing the results of array-based binding assays (e.g., hybridization reactions).

73 Claims, No Drawings

METHODS FOR ARRAY-BASED COMPARITIVE BINDING ASSAYS

TECHNICAL FIELD

This invention relates to molecular biology, genetic diagnostics and array, or "biochip," technology. In particular, the invention provides computer systems, computer program products and methods for in silico array-based methods for determining the relative amount of biological molecules (e.g., nucleic acid sequences) in two or more samples. The invention also provides novel arrays comprising immobilized calibration molecules (e.g., nucleic acids) for normalizing the results of array-based binding assays (e.g., hybridization reactions).

BACKGROUND

Comparative genomic hybridization (CGH) was first developed for genome-wide analysis of DNA sequence copy number in a single experiment, see, e.g., Pinkel (1998) Nat. Genet. 20:207–211. Genomic DNA microarray based comparative genomic hybridization (CGH) has the potential to solve many of the limitations of traditional CGH method, which relies on comparative hybridization on individual metaphase chromosomes. CGH can be used to determine the relative copy number of nucleic acid sequences between two samples. CGH can also be used to precisely map chromosomal abnormalities associated with disease.

In metaphase CGH, multi-megabase fragments of different samples of genomic DNA are labeled and hybridized to a fixed chromosome. See, e.g., Breen (1999) J. Med. Genetics 36:511–517; Rice (2000) Pediatric Hematol. Oncol. 17:141–147. The CGH can compare known or normal DNA to a test sample, e.g., DNA from a possible tumor cell. Signal differences between known and test samples are detected and measured. In this way, missing, amplified, or unique sequences in the test sample, as compared to "normal," can be detected by the fluorescence ratio of normal control to test genomic DNA. In metaphase CGH, the target sites (on the fixed chromosome) are saturated by an excess amount of soluble, labeled genomic DNA.

In contrast to metaphase CGH, where the immobilized genomic DNA is a metaphase spread, in array-based CGH method the immobilized nucleic acids are arranged as an array, on, e.g., a biochip or a microarray platform. See, e.g., U.S. Pat. No. 5,830,645. Another difference is that in array-based CGH the immobilized genomic DNA is in molar excess as compared to the copy number of labeled (test and control) genomic nucleic acid. In array-based CGH, test and control, or "normal," nucleic acids are mixed together and applied to the array, or "biochip." In traditional CGH, because test and sample nucleic acids are mixed together before their application to the array they must be differentially labeled. Both the mixing together of samples and the use of different labels in the samples to be compared can result in artifacts and erroneous results.

SUMMARY

The invention provides computer systems, computer program products and methods, including computer-implemented methods, for an array-based determination of the relative amount of biological molecules, e.g., nucleic acid sequences or polypeptides, in two or more samples.

The invention provides an in silico, array-based method for determining the relative amount of a biological molecule, e.g., a nucleic acid sequence, in two or more samples, the method comprising: (a) providing a first array comprising a plurality of nucleic acid segments, wherein each nucleic acid segment is immobilized to a discrete and known spot on a first substrate surface to form a first array of nucleic acid segments; (b) providing (at least) a second array comprising a plurality of nucleic acid segments, wherein each nucleic acid segment is immobilized to a discrete and known spot on a second substrate surface to form a second array of nucleic acid segments, and the nucleic acid segments immobilized on the second array comprise substantially the same plurality of nucleic acid segments arrayed in step (a); (c) providing a first sample comprising a plurality of nucleic acid sequences comprising a detectable label; (d) providing a second sample comprising a plurality of nucleic acid sequences comprising a detectable label; (e) contacting the first sample of step (c) with the first array of step (a) under conditions wherein the labeled nucleic acid can specifically hybridize to a nucleic acid segment immobilized on the first array; (f) contacting the second sample of step (d) with the second array of step (b) under the same conditions as in step (e), thereby allowing the labeled nucleic acid to specifically hybridize to a nucleic acid segment immobilized on the second array; (g) identifying which spots on the first and the second substrate surfaces are specifically hybridized to a labeled nucleic acid segment and measuring the amount of label on each spot; and, (h) comparing the amount of labeled nucleic acid sequence bound by specific hybridization to a nucleic acid segment immobilized on the first array to the amount of labeled nucleic acid sequence bound by specific hybridization to the same nucleic acid segment immobilized on the second array, thereby determining the relative amount of a nucleic acid sequence complementary to the same nucleic acid segment in the first sample compared to the second sample.

In alternative aspects, the biological molecule comprises a nucleic acid, e.g., an oligonucleotide, a lipid, a polysaccharide, a polypeptide (e.g., a peptide), or an analog or a mimetic thereof, or a combination thereof. The nucleic acid can comprise a DNA (e.g., a genomic DNA or a cDNA), an RNA (e.g., an mRNA, rRNA, and the like) or an analog or a mimetic thereof or a combination thereof. The nucleic acid can further comprise a telomeric structure or a chromatin structure. Analogs and mimetics can include small molecules, as discussed below. In alternative aspects, the array-immobilized nucleic acid segments comprise cloned genomic nucleic acid, cDNA, synthetic nucleic acid, and the like. The array-immobilized genomic nucleic acid can comprise a substantially complete chromosome or a known subset of a chromosome. The genomic nucleic acid can comprise a substantially complete genome or a known subset of a genome.

The array-immobilized nucleic acid can be derived from the transcripts of or from the genome of any cell, for example, a genotypically and/or phenotypically normal cell. The nucleic acid can be derived from a genome of a mammalian cell, such as a human cell.

As noted above, in the methods a plurality of biological molecules (e.g., nucleic acids) in at least two samples are labeled, e.g., sample nucleic acids comprise a detectable label. In one aspect, a plurality of labeled nucleic acid sequences comprises sequences the same or complementary to a subset or to substantially all of the transcripts expressed by a cell. The plurality of labeled nucleic acid sequences in one, several or all of the samples can comprise genomic sequences. In one aspect, the plurality of labeled nucleic acid sequences comprise a substantially complete chromosome or a known subset of a chromosome. The plurality of labeled nucleic acid sequences can comprise a substantially complete genome or a known subset of a genome. In one aspect, the array-immobilized nucleic acid comprises a substantially complete genome or a known subset of a genome and the plurality of labeled nucleic acid sequences from each sample comprise a substantially complete of the genome or a known subset of the genome, thereby the method is performing a comparative genomic hybridization (CGH).

In one aspect, biological molecules (e.g., nucleic acids) from the first sample are derived from a cell with a normal genotype and the nucleic acid from the second sample is derived from a cell with an abnormal genotype. Alternatively, the biological molecules (e.g., nucleic acids) from the first sample can be derived from a cell with a normal phenotype and the biological molecules (e.g., nucleic acids) from the second sample can be derived from a cell with an abnormal phenotype. The abnormal phenotype can comprise a disease phenotype or a neoplastic or hyperplastic phenotype. The neoplastic phenotype can be any cancer or neoplastic or hyperplastic condition, e.g., breast cancer, skin cancer, bone cancer.

In one aspect, the biological molecules (e.g., nucleic acids) from the first sample are derived from an unstimulated cell and biological molecules (e.g., nucleic acids) from the second sample are derived from an unstimulated cell after stimulation. The biological molecules (e.g., nucleic acids) from the first sample can be derived from an undifferentiated cell and the biological molecules (e.g., nucleic acids) from the second sample can be derived from the undifferentiated cell after stimulation. The biological molecules (e.g., nucleic acids) from the first sample can be derived from a normal cell and the biological molecules (e.g., nucleic acids) from the second sample can be derived from the normal cell after an injury. The biological molecules (e.g., nucleic acids) from the first sample can be derived from a normal cell and the biological molecules (e.g., nucleic acids) from the second sample can be derived from the normal cell after an environmental stress. The environmental stress can comprise a high or a low or a change in temperature. The environmental stress can comprise an exposure to a chemical, such as a carcinogen, a drug or a medicine.

In alternative aspects, the nucleic acid comprises a DNA, including a genomic DNA, cDNA, expressed sequence tags (EST), analogs or mimetics thereof, synthetic DNA and the like. The nucleic acid can comprise an RNA (e.g., an mRNA, rRNA, and the like) or an analog or a mimetic thereof or a combination thereof. In one aspect, an immobilized nucleic acid segment comprises nucleic acid, e.g., genomic DNA, cloned in a construct comprising an artificial chromosome. The artificial chromosome can comprise a bacterial artificial chromosome (BAC), a human artificial chromosome (HAC) a yeast artificial chromosome (YAC), a transformation-competent artificial chromosome (TAC) or a bacteriophage P1-derived artificial chromosome (PAC). The array-immobilized nucleic acid segment can be cloned in a construct comprising a vector, such as a cosmid vector, a plasmid vector, a phage or a viral vector. The array-immobilized nucleic acid segment can be between about 50 kilobases (0.5 megabase) to about 500 kilobases (5 megabases) in length, between about 100 kilobases (1 megabase) to about 400 kilobases (4 megabases) in length, or, is about 300 kilobases (3 megabases) in length.

In alternative aspects, labeled biological molecules (e.g., nucleic acids) are derived from a body fluid sample, a cell sample or a tissue sample. The labeled biological molecules (e.g., nucleic acids) can be derived from a cancer cell or a tumor cell sample. In alternative aspects, a labeled biological molecule (e.g., nucleic acid) in one sample is derived from a biopsy sample, a blood sample, a urine sample, a saliva sample or a CSF sample.

In one aspect, the method further comprises a washing step. In the washing step biological molecules (e.g., nucleic acids) not specifically bound (e.g., hybridized) to array-immobilized biological molecules (e.g., nucleic acids) are removed before the identifying step (g). The washing step can comprise use of a solution comprising a salt concentration of about 0.02 molar at pH 7 at a temperature of at least about 50° C. The washing step can comprise use of a solution comprising a salt concentration of about 0.15 M at a temperature of at least about 72° C. for about 15 minutes. The washing step can comprise use of a solution comprising a salt concentration of about 0.2×SSC at a temperature of at least about 50° C. for at least about 15 minutes.

In one aspect, all sample biological molecules (e.g., nucleic acids) comprise the same label. For example, the first sample biological molecules (e.g., nucleic acids) and the second sample biological molecules (e.g., nucleic acids) can comprise the same label. Alternatively, first sample biological molecules (e.g., nucleic acids) and second sample (and third sample, etc.) biological molecules (e.g., nucleic acids) can comprise different labels. The sample biological molecules (e.g., nucleic acids) can be labeled with any detectable label, e.g., a fluorochrome, a chemiluminescent label, and equivalents. In alternative aspects, the detectable label comprises a fluorescent label, such as a Cy5™ or equivalent, a Cy3™ or equivalents; and, a rhodamine, a fluorescein or an aryl-substituted 4,4-difluoro-4-bora-3a, 4a-diaza-s-indacene dye or equivalents.

The methods of the invention can further comprise providing a third (or fourth, or fifth, etc.) array comprising a plurality of biological molecules (e.g., nucleic acids), wherein each biological molecules (e.g., nucleic acids) is immobilized to a discrete and known spot on a third (or fourth, or fifth, etc.) substrate surface to form a third (or fourth, or fifth, etc.) array of biological molecules (e.g., nucleic acids), and the biological molecules (e.g., nucleic acids) immobilized on the third (or fourth, or fifth, etc.) array comprise substantially the same plurality of biological molecules (e.g., nucleic acids) arrayed in step (a), and a third (or fourth, or fifth, etc.) sample comprising a plurality of biological molecules (e.g., nucleic acids) comprising a detectable label; contacting the third sample with the third array under the same conditions as in step (e), thereby allowing the labeled biological molecules (e.g., nucleic acids) to specifically bind (e.g., hybridize) to a biological molecules (e.g., nucleic acids) immobilized on the third (or fourth, or fifth, etc.) array; identifying which spots on the first, second and third (or fourth, or fifth, etc.) substrate surfaces are specifically bound (e.g., hybridized) to a labeled biological molecules (e.g., nucleic acids) and measuring the amount of label on each spot; and, comparing the amount of labeled biological molecules (e.g., nucleic acids) bound by specific binding (e.g., hybridization) to the same biological molecule (e.g., nucleic acid) immobilized on the first array, the second array and the third array (or fourth, or fifth, etc. arrays), thereby determining the relative amount of a biological molecule (e.g., nucleic acid) in the first, second and third (or fourth, or fifth, etc.) samples. In one aspect, the third, fourth, fifth, etc. arrays are contacted with duplicates or triplicates, etc., of biological molecule (e.g., nucleic acid) samples.

The methods can further comprise the step of blocking the ability of repetitive nucleic acid sequences to hybridize (i.e., blocking "hybridization capacity") in the immobilized nucleic acid segments. The methods can also further comprise the step of blocking the hybridization capacity of repetitive nucleic acid sequences in the sample nucleic acid sequences by mixing the sample nucleic acid sequences with unlabeled (or alternatively labeled) repetitive nucleic acid sequences. In one aspect, the sample nucleic acid sequences are first mixed with repetitive nucleic acid sequences before the step comprising contacting with the array-immobilized nucleic acid segments. The repetitive nucleic acid sequences can be unlabeled. The repetitive nucleic acid sequences can comprise Cot-1 DNA or equivalent, SST sequences or equivalent, or salmon sperm DNA or equivalent, or a combination thereof.

The invention provides an in silico, array-based method for performing comparative genomic hybridization (CGH), the method comprising: (a) providing a first array comprising a plurality of genomic nucleic acid segments, wherein each nucleic acid segment is immobilized to a discrete and known spot on a first substrate surface to form a first array of genomic nucleic acid segments and the plurality of genomic nucleic acid segments comprise a substantially complete genome or a known subset of a genome; (b) providing a second array comprising substantially the same plurality of genomic nucleic acid segments arrayed in step (a), wherein each nucleic acid segment is immobilized to a discrete and known spot on a second substrate surface to form a second array of genomic nucleic acid segments; (c) providing a first sample comprising a plurality of genomic nucleic acid sequences comprising a detectable label; (d) providing a second sample comprising a plurality of genomic nucleic acid sequences comprising a detectable label; (e) contacting the first sample of step (c) with the first array of step (a) under conditions wherein the labeled nucleic acid can specifically hybridize to the nucleic acid segments immobilized on the first array; (f) contacting the second sample of step (d) with the second array of step (b) under the same conditions as in step (e), thereby allowing the labeled nucleic acid to specifically hybridize to the nucleic acid segments immobilized on the second array; (g) identifying which spots on the first and the second substrate surfaces are specifically hybridized to a labeled nucleic acid segment and measuring the amount of label on each spot; and, (h) comparing the amount of labeled nucleic acid sequence bound by specific hybridization to an immobilized nucleic acid in the first array to the amount of labeled nucleic acid sequence bound by specific hybridization to the same (i.e., the equivalent) immobilized nucleic acid in the second array, thereby determining the relative amount of a nucleic acid sequence complementary to the nucleic acid in the first sample compared to the second sample and performing a comparative genomic hybridization.

The invention provides an in silico, array-based method of determining one or more variations in copy numbers of biological molecules in a first sample relative to copy numbers of substantially identical biological molecules in at least a second sample, the method comprising the steps of: (a) providing a first array and at least a second array, each comprising a plurality of immobilized biological molecules, wherein the biological molecules are immobilized to discrete and known spots on a substrate surface to form at least two arrays of biological molecules, and the second array comprises substantially the same plurality of biological molecules immobilized in the first array; (a) providing at least two samples comprising biological molecules and labeling biological molecules from each sample, wherein biological molecules in all samples comprise the same label or biological molecules in the first sample comprise a different label than biological molecules in the second label; (b) contacting the first sample of labeled biological molecules to the first array and the second sample of labeled biological molecules to the second array under conditions wherein the labeled sample biological molecules can specifically bind to the immobilized biological molecules; and (c) detecting the amount of label associated with each spot and comparing the amount of label associated with an immobilized biological molecule in the first array to the amount of label associated with the same immobilized biological molecule in the second array, thereby determining the amount of immobilized biological molecule in the first sample relative to the second sample.

The invention provides an in silico, array-based method of determining one or more variations in copy numbers of unique nucleic acid sequences in a first sample relative to copy numbers of substantially identical sequences in at least a second sample, the method comprising the steps of: (a) providing a first array and at least a second array, each comprising a plurality of immobilized nucleic acids, wherein the nucleic acids are immobilized to discrete and known spots on a substrate surface to form at least two arrays of nucleic acid segments, and the second array comprises substantially the same plurality of nucleic acid segments immobilized in the first array; (a) providing at least two nucleic acid samples and labeling the nucleic acid from each sample, wherein nucleic acids in all samples comprise the same label or the nucleic acid in the first sample comprises a different label than the nucleic acid in the second label; (b) contacting the first sample of labeled nucleic acid to the first array and the second sample of labeled nucleic acid to the second array under conditions wherein the labeled nucleic acids can specifically hybridize to the immobilized nucleic acids immobilized on the arrays; and, (c) detecting the amount of label associated with each spot and comparing the amount of label associated with a nucleic acid sequence in the first array to the amount of label associated with the same nucleic acid sequence in the second array, thereby determining one or more variations in copy numbers of unique nucleic acid sequences in a first sample relative to copy numbers of substantially identical (e.g., complementary) sequences in at least a second sample.

The method of the invention can further comprise determining the ratio of the amount of label associated with a biological molecule (e.g., a nucleic acid sequence) in the first and the second arrays, thereby determining a ratio of signal intensity.

The methods of the invention can further comprise determining the amount of a calibration molecule, wherein a known amount of a calibration molecule is spotted on each array. In one aspect, the methods comprise determining the average copy number of a calibration sequence, wherein a known amount of calibration sequence is mixed with the first and the second samples, and the calibration sequence is substantially the same as a unique sequence in an immobilized nucleic acid sequence present in both arrays. A known amount of a calibration molecule-binding composition can be mixed with the first and the second samples. Each array can comprise a calibration spot, wherein the calibration spot comprises a biological molecule from each spot on an array.

The method can further comprise determining the average copy number of a calibration sequence, wherein a known amount of a calibration sequence is spotted on each array, and (i) a known amount of a calibration sequence is mixed with the first and the second samples the calibration sequence is derived from an different source from which the sample nucleic acids were derived, or, (ii) the calibration sequences spotted on the array comprise at least one sequence of a nucleic acid from each of the array spots.

The method can further comprise determining whether the expected ratio of the known amount of calibration sequence is detected on the two arrays, and, if the expected ratio is not detected, determining a correction factor. The method can further comprise normalizing the ratio of the amount of label associated with the nucleic acid sequence in the first and the second array by adjusting the ratio by a figure representing the difference between the expected calibration sequence ratio and the detected of calibration sequence ratio on the (at least) two arrays. The methods of the invention further comprise determining (and outputting or displaying when a computer-implemented method) calibration, or normalization, curves based on binding to "calibration" or "control" spots, as discussed in detail, below.

In one aspect, the calibration molecule is spotted in titrated concentrations on each of the arrays. The methods can further comprise determining whether the expected ratio of the known amount of calibration molecule is detected on the two arrays. The methods can further comprise normalizing the ratio of the amount of label associated with a biological molecule in the first and second arrays by adjusting the ratio by a figure representing the difference between the expected ratio of calibration molecules and the detected ratio of calibration molecules on the two arrays.

The invention provides a kit comprising the following components: (a) (i) at least two arrays, each comprising a plurality of biological molecules, wherein each biological molecules is immobilized to a discrete and known spot on a substrate surface to form an array, or (ii) a biochip comprising a first substrate surface comprising a first array and a second substrate surface comprising a second array, wherein the first and second arrays are separated by a hydrophobic barrier such that a first sample can be applied to the first array at the same time a second sample is applied to the second array without the two samples mixing together; and, (b) instructions for using the arrays comprising a method of the invention.

The invention provides a kit comprising the following components: (a) at least two arrays, each comprising a plurality of cloned genomic nucleic acid segments, wherein each genomic nucleic acid segment is immobilized to a discrete and known spot on a substrate surface to form an array and the cloned genomic nucleic acid segments comprise a substantially complete genome or a known subset of a genome; and, (b) instructions for using the array comprising a method of the invention. The kit can further comprise materials to prepare a sample comprising a nucleic acid (e.g., a genomic DNA) for application to the array. This can includes, e.g., instructions and compositions to fragment/cut and/or label the nucleic acid. The kit can further comprise a sample of wild type, or normal, nucleic acid. The wild type, or normal, nucleic acid can comprise a label. The wild type, or normal, nucleic acid of the kit can comprise a human wild type genomic nucleic acid. The kit can include an array comprising a G-CHIP™, a mouse BAC array or a human BAC Array.

The invention provides a computer program product in a computer readable medium for determining the relative amount of a biological molecule (e.g., a nucleic acid) in two or more samples comprising: a computer useable medium comprising a computer readable program code embodied therein, wherein the computer program product is capable of determining the relative amount of a biological molecule (e.g., a nucleic acid) in two or more samples by a process comprising the following steps: (a) collecting data comprising which spots on a first array substrate surface and at least a second array substrate surface are specifically bound (e.g., hybridized) to a labeled biological molecule (e.g., a nucleic acid) and the amount of labeled biological molecule (e.g., nucleic acid) on each spot, wherein the data is generated by a method of the invention; and, (b) comparing the amount of labeled biological molecule (e.g., nucleic acid) bound (e.g., by specific hybridization) to a biological molecule (e.g., nucleic acid) immobilized on the first array to the amount of labeled biological molecule (e.g., nucleic acid) bound (e.g., by specific hybridization) to the same biological molecule (e.g., nucleic acid) immobilized on the second array by comparing the data collected in step (a), thereby determining the relative amount of a biological molecule (e.g., nucleic acid) in the first sample compared to the second sample.

The invention provides a computer-implemented method for determining the relative amount of a biological molecule (e.g., nucleic acid) in two or more samples comprising the following steps: (a) identifying which spots on a first array substrate surface and at least a second array substrate surface are specifically bound (e.g. hybridized) to a labeled biological molecule (e.g., nucleic acid) and the amount of labeled biological molecule (e.g., nucleic acid) on each spot, wherein the data is generated by a method of the invention, and communicating this data to a computer program product; (b) comparing the amount of labeled biological molecule (e.g., nucleic acid) bound (e.g., by specific hybridization) to a biological molecule (e.g., nucleic acid) immobilized on the first array to the amount of labeled biological molecule (e.g., nucleic acid) bound (e.g., by specific hybridization) to the same biological molecule (e.g., nucleic acid) immobilized on the second array by comparing the data communicated in step (a) and using a computer program product of the invention, thereby determining the relative amount of a biological molecule (e.g., nucleic acid) in the first sample compared to the second sample.

The invention provides a computer system, comprising: (a) a processor; and, (b) a computer program product of the invention.

The invention provides an array for determining the relative amount of a biological molecule (e.g., a nucleic acid) a sample comprising a plurality of biological molecules immobilized to a plurality of discrete and known spots on a substrate surface to form an array of biological molecules, wherein the array of spots comprises a plurality of test spots (i.e., for binding, e.g., by hybridization, to molecules in a sample) and at least one calibration spot, and the calibration spot comprises at least one copy of a sequence from each test spot on the array. In one aspect, the calibration spot comprises an equimolar mixture of all the biological molecules spotted on the array. The array can further comprise at least a second calibration spot. The additional calibration spots can comprise at least one copy of a sequence from each test spot on the array. In one aspect, additional calibration spots comprise an equimolar dilution of (or increase in) the mixture of biological molecules spotted on a first calibration spot. In one aspect, the array comprises a plurality of calibration spots. Each calibration spot can represent a different equimolar dilution of the mixture of biological molecules spotted on the array. As discussed in detail, below, the "control spots" or "calibration spots" are used for "normalization" of data generated in one or more arrays, e.g., in the in silico array-based methods of the invention. Control spots can provide a consistent result independent of the labeled sample bound, e.g., hybridized, to the array. The control spots can be used to generate a "normalization" or "calibration" curve to offset possible intensity errors between the two or more arrays. In one aspect of the methods of the invention, "calibration" curves are generated using arrays comprising a plurality of "control spots." The computer-implemented methods, computer program products and computer systems of the invention can calculate and display calibration/normalization curves from binding (e.g., hybridization) data read from control spots from two or more arrays.

In one aspect, the array of the invention comprises a first substrate surface comprising a first array and a second substrate surface comprising a second array, wherein the first and second arrays are separated by a hydrophobic barrier such that a first sample can be applied to the first array at the same time a second sample is applied to the second array without the two samples mixing together, and the first and the second arrays comprise the same calibration spots.

In one aspect, the biological molecule comprises a nucleic acid, such as a DNA (e.g., cDNA or a genomic DNA) or an RNA (e.g., mRNA). Alternatively, the biological molecule can comprises a polypeptide, a peptide, a lipid or a polysaccharide.

The invention provides a multiplexed system for performing comparative genomic hybridization (CGH) using an array comprising: (a) an array comprising (i) a plurality of biological molecules immobilized to a plurality of discrete and known spots on a substrate surface to form an array of biological molecules, wherein the array of spot comprises a plurality of test spots and at least one calibration spot, and the calibration spot comprises at least one copy of a sequence from each test spot on the array, or (ii) a first substrate surface comprising a first array and a second substrate surface comprising a second array, wherein the first and second arrays are separated by a hydrophobic barrier such that a first sample can be applied to the first array at the same time a second sample is applied to the second array without the two samples mixing together, and the first and the second arrays comprise the same calibration spots; (b) a device for detecting a detectable label, wherein the device can measure which detectable labels are on which spots on the substrate surface.

The details of one or more embodiments of the invention are set forth in the accompanying drawings and the description below. Other features, objects, and advantages of the invention will be apparent from the description and drawings, and from the claims.

All publications, GenBank Accession references (sequences), ATCC Deposits, patents and patent applications cited herein are hereby expressly incorporated by reference for all purposes.

DETAILED DESCRIPTION

The invention provides in silico, array-based methods for determining the relative amount of a binding molecule (e.g., nucleic acid sequence) in two or more samples. Also provided are computer-implemented methods, computer program products and computer systems for determining the relative amount of a binding molecule (e.g., nucleic acid sequence) in two or more samples.

The invention also provides novel arrays comprising immobilized calibration sequences for normalizing the results of array-based hybridization reactions.

In practicing the compositions and methods of the invention, two or more samples of labeled biological molecules (e.g. nucleic acid) are applied to two or more arrays, where the arrays have substantially the same complement of immobilized binding molecule (e.g., immobilized nucleic acid capable of hybridizing to labeled sample nucleic acid). In other words, when practicing the compositions and methods of the invention, different biological molecules (e.g. nucleic acid) samples are not mixed together. They are applied to an array surface(s) separately.

While the invention is not limited to any particular mechanism of action or advantage, not having to mix two samples (e.g., a test and a "normal" sample) together avoids interaction between sample molecules (including the labeled nucleic acids) that may create false/inaccurate results or artifacts. Additionally, practicing the compositions and methods of the invention allows use of the same detectable label for every sample, further avoiding sample-induced artifacts by mixing different detectable labels.

The two or more arrays can, of course, be simply multiple copies of the same array. However, to practice the compositions and methods of the invention it is only necessary that the arrays have substantially the same complement of immobilized biological molecules (e.g. nucleic acid). Because each "spot" or "biosite" on the array has similar biological molecules (e.g. nucleic acids of the same sequence) and the biological molecules (e.g. nucleic acid) in each spot is known, as is typical of nucleic acid and other arrays, it is not necessary that the multiple arrays used in the invention be identical in configuration. Thus, in one aspect, multiple biological molecules (e.g. nucleic acid) samples are comparatively bound to the array (e.g., hybridized simultaneously).

Alternatively, because in one aspect of the invention biological molecules (e.g. nucleic acid) samples are applied to an array separately and are not mixed, the application of samples to arrays need not be done simultaneously. Thus, the second array can in fact simply be the first array reused, thus, the second or third or additional arrays can be a "constructive second (or third, etc.) array."

Alternatively, in one aspect of the invention a single "biochip" comprising at least two complements of immobilized biological molecules (e.g. nucleic acid) is used. Each set of immobilized, arrayed labeled biological molecules (e.g. nucleic acid) complements are separated, e.g., by a physical separator or a hydrophobic boundary. Thus, in this aspect, although biological molecules (e.g. nucleic acid) samples are applied to the same biochip simultaneously they are not mixed together because they are applied to separated chambers or wells. Each chamber or well can comprise an array where each array has substantially the same complement of immobilized biological molecules (e.g. nucleic acid), as discussed above. This would allow for the analysis to be done on a single biochip, or "multi-array." Because each complement of spotted biological molecules (e.g. nucleic acid) are in separated areas of the chip, e.g., wells or chambers, the system would still behave as two (or more) separate arrays. In another aspect, this physical separation is achieved by generating a hydrophobic boundary that could prevent the samples from flowing from one array or "biological molecules (e.g. nucleic acid) complement" to another. Exemplary welled array systems include multi-welled titer plates. Thus, in one aspect, multiple biological molecules (e.g. nucleic acid) complements or arrays are constructed on one multi-array plate. Only one sample is place in one well or chamber.

Definitions

Unless defined otherwise, all technical and scientific terms used herein have the meaning commonly understood by a person skilled in the art to which this invention belongs.

As used herein, the following terms have the meanings ascribed to them unless specified otherwise.

The terms "array" or "microarray" or "biochip" or "chip" as used herein refer to articles of manufacture or devices comprising a plurality of immobilized target elements, each target element comprising a "cluster," "biosite," "spot" or defined area comprising a particular composition, such as a biological molecule, e.g., a nucleic acid molecule or polypeptide, immobilized to a solid surface, as discussed in further detail, below.

The term "biological molecule" includes all naturally found molecules, including nucleic acids, polypeptides, lipids, polysaccharides, and molecules isolated from, derived from or based on a naturally found molecules, including small molecules, and analogs and mimetics thereof.

The term "aryl-substituted 4,4-difluoro-4-bora-3a, 4a-diaza-s-indacene dye" as used herein includes all "boron dipyrromethene difluoride fluorophore" or "BODIPY" dyes and "dipyrrometheneboron difluoride dyes" (see, e.g., U.S. Pat. No. 4,774,339), or equivalents, are a class of fluorescent dyes commonly used to label nucleic acids for their detection when used in hybridization reactions; see, e.g., Chen (2000) J. Org Chem. 65:2900–2906: Chen (2000) J. Biochem. Biophys. Methods 42:137–151. See also U.S. Pat. Nos. 6,060,324; 5,994,063; 5,614,386; 5,248,782; 5,227, 487; 5,187,288.

The terms "cyanine 5" or "Cy5™" and "cyanine 3" or "Cy3™" refer to fluorescent cyanine dyes produced by Amersham Pharmacia Biotech (Piscataway, N.J.) (Amersham Life Sciences, Arlington Heights, Ill.), as described in detail, below, or equivalents. See U.S. Pat. Nos. 6,027,709; 5,714,386; 5,268,486; 5,151,507; 5,047,519. These dyes are typically incorporated into nucleic acids in the form of 5-amino-propargyl-2'-deoxycytidine 5'-triphosphate coupled to Cy5™ or Cy3™.

The term "fluorescent dye" as used herein includes all known fluors, including rhodamine dyes (e.g., tetramethylrhodamine, dibenzorhodamine, see, e.g., U.S. Pat. No. 6,051,719); fluorescein dyes; "BODIPY" dyes and equivalents (e.g., dipyrrometheneboron difluoride dyes, see, e.g., U.S. Pat. No. 5,274,113); derivatives of 1-[isoindolyl] methylene-isoindole (see, e.g., U.S. Pat. No. 5,433,896); and all equivalents. See also U.S. Pat. Nos. 6,028,190; 5,188, 934.

The terms "specifically hybridize to," "hybridizing specifically to," "specific hybridization" and "selectively hybridize to," as used herein refer to the binding, duplexing, or hybridizing of a nucleic acid molecule preferentially to a particular nucleotide sequence under stringent conditions. The term "stringent conditions" refers to conditions under which a probe will hybridize preferentially to its target subsequence; and to a lesser extent to, or not at all to, other sequences. A "stringent hybridization" and "stringent hybridization wash conditions" in the context of nucleic acid hybridization (e.g., as in array, Southern or Northern hybridizations) are sequence dependent, and are different under different environmental parameters. Alternative hybridization conditions that can be used to practice the invention are described in detail, below. In alternative aspects, the hybridization and/or wash conditions are carried out under moderate conditions, stringent conditions and very stringent conditions, as described in further detail, below. Alternative wash conditions are also used in different aspects, as described in further detail, herein.

The phrases "labeled biological molecule" or "labeled with a detectable composition" or "labeled with a detectable moiety" as used herein refer to a biological molecule, e.g., a nucleic acid, comprising a detectable composition, i.e., a label, as described in detail, below. The label can also be another biological molecule, as a nucleic acid, e.g., a nucleic acid in the form of a stem-loop structure as a "molecular beacon," as described below. This includes incorporation of labeled bases (or, bases which can bind to a detectable label) into the nucleic acid by, e.g., nick translation, random primer extension, amplification with degenerate primers, and the like. Any label can be used, e.g., chemiluminescent labels, radiolabels, enzymatic labels and the like. The label can be detectable by any means, e.g., visual, spectroscopic, photochemical, biochemical, immunochemical, physical, chemical and/or chemiluminescent detection. The invention can use arrays comprising immobilized nucleic acids comprising detectable labels.

The term "nucleic acid" as used herein refers to a deoxyribonucleotide (DNA) or ribonucleotide (RNA) in either single- or double-stranded form. The term encompasses nucleic acids containing known analogues of natural nucleotides. The term encompasses mixed oligonucleotides comprising an RNA portion bearing 2'-O-alkyl substituents conjugated to a DNA portion via a phosphodiester linkage, see, e.g., U.S. Pat. No. 5,013,830. The term also encompasses nucleic-acid-like structures with synthetic backbones. DNA backbone analogues used to make or practice the invention include phosphodiester, phosphorothioate, phosphorodithioate, methylphosphonate, phosphoramidate, alkyl phosphotriester, sulfamate, 3'-thioacetal, methylene (methylimino), 3'-N-carbamate, morpholino carbamate, and peptide nucleic acids (PNAs); see Oligonucleotides and Analogues, a Practical Approach, edited by F. Eckstein, In Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923–1937; Antisense Research and Applications (1993, CRC Press). PNAs contain non-ionic backbones, such as N-(2-aminoethyl) glycine units. Phosphorothioate linkages are described, e.g., by U.S. Pat. Nos. 6,031,092; 6,001,982; 5,684,148; see also, WO 97/03211; WO 96/39154; Mata (1997) Toxicol. Appl. Pharmacol. 144:189–197. Other synthetic backbones encompassed by the term include methyl-phosphonate linkages or alternating methylphosphonate and phosphodiester linkages (see, e.g., U.S. Pat. No. 5,962,674; Strauss-Soukup (1997) Biochemistry 36:8692–8698), and benzylphosphonate linkages (see, e.g., U.S. Pat. No. 5,532,226; Samstag (1996) Antisense Nucleic Acid Drug Dev 6:153–156). The term nucleic acid is used interchangeably with gene, DNA, RNA, cDNA, mRNA, oligonucleotide primer, probe and amplification product.

The terms "sample comprising a plurality of biological molecules," "sample of targets" or "sample of nucleic acids" as used herein refer to a sample comprising a biological molecule, e.g., a polypeptide, a lipid, a polysaccharide, a DNA or RNA, or nucleic acid representative of DNA or RNA isolated from a natural source in a form suitable for hybridization (e.g., as a soluble aqueous solution) to another nucleic acid or polypeptide or combination thereof (e.g., immobilized probes). The nucleic acid may be isolated, cloned or amplified; it may be, e.g., genomic DNA, mRNA, or cDNA from substantially an entire genome, substantially all or part of a particular chromosome, or selected sequences (e.g. particular promoters, genes, amplification or restriction fragments, cDNA, etc.). The nucleic acid sample may be extracted from particular cells or tissues. The cell or tissue sample from which the nucleic acid sample is prepared is typically taken from a patient suspected of having a genetic defect or a genetically-linked pathology or condition, e.g., a cancer, associated with genomic nucleic acid base substitutions, amplifications, deletions and/or translocations. Methods of isolating cell and tissue samples are well known to those of skill in the art and include, but are not limited to, aspirations, tissue sections, needle biopsies, and the like. Frequently the sample will be a "clinical sample" which is a sample derived from a patient, including sections of tissues such as frozen sections or paraffin sections taken for histological purposes. The sample can also be derived from supernatants (of cells) or the cells themselves from cell cultures, cells from tissue culture and other media in which it may be desirable to detect chromosomal abnormalities or determine amplicon copy number. In some cases, the nucleic acids may be amplified using standard techniques such as PCR, prior to the hybridization. The probe an be produced from and collectively can be representative of a source of nucleic acids from one or more particular (pre-selected) portions of, e.g., a collection of polymerase chain reaction (PCR) amplification products, substantially an entire chromosome or a chromosome fragment, or substantially an entire genome, e.g., as a collection of clones, e.g., BACs, PACs, YACs, and the like (see below). The probe or genomic nucleic acid sample may be processed in some manner, e.g., by blocking or removal of repetitive nucleic acids or by enrichment with selected nucleic acids.

The terms "polypeptide," "protein," and "peptide" include "analogs," or "conservative variants" and "mimetics" or "peptidomimetics" with structures and activity that substantially correspond to the polypeptide from which the variant was derived, as discussed in detail, below.

The term "small molecule" means any synthetic small molecule, such as an organic molecule or a synthetic molecule, such as those generated by combinatorial chemistry methodologies. These small molecules can be synthesized using a variety of procedures and methodologies, which are well described in the scientific and patent literature, e.g., Organic Syntheses Collective Volumes, Gilman et al. (Eds) John Wiley & Sons, Inc., NY; Venuti (1989) Pharm Res. 6:867–873. Synthesis of small molecules, as with all other procedures associated with this invention, can be practiced in conjunction with any method or protocol known in the art. For example, preparation and screening of combinatorial chemical libraries are well known, see, e.g., U.S. Pat. Nos. 6,096,496; 6,075,166; 6,054,047; 6,004,617; 5,985,356; 5,980,839; 5,917,185; 5,767,238.

The term "SST sequences" as used herein means repetitive sequences in a genome identified by a fast Sensitive Search Tool (SST), as described below.

As used herein, the terms "computer" and "processor" are used in their broadest general contexts and incorporate all such devices. The methods of the invention can be practiced using any computer/processor and in conjunction with any known software or methodology. For example, a computer/processor can be a conventional general-purpose digital computer, e.g., a personal "workstation" computer, including conventional elements such as microprocessor and data transfer bus. The computer/processor can further include any form of memory elements, such as dynamic random access memory, flash memory or the like, or mass storage such as magnetic disc optional storage.

Generating and Manipulating Nucleic Acids

The computer program products, systems and methods of the invention used to determining the relative amount of a nucleic acid sequence in two or more samples comprise arrays comprising a plurality of nucleic acid segments. The sample or the immobilized nucleic acid can be representative of genomic DNA, including defined parts of, or entire, chromosomes, or entire genomes. Alternatively, the nucleic acids can be cDNA, expressed sequence tags (EST), analogs or mimetics thereof, synthetic DNA, RNA (e.g., an mRNA, rRNA, and the like) or analogs or mimetics thereof or combinations thereof.

In several aspects, the computer program products, systems and methods of the invention are used in comparative genomic hybridization (CGH) reactions on arrays. The invention can be practiced in conjunction with any method or protocol or device known in the art, which are well described in the scientific and patent literature; see, e.g., U.S. Pat. Nos. 6,159,685; 5,830,645; 5,976,790.

General Techniques

The nucleic acids used to practice this invention, whether RNA, cDNA, genomic DNA, vectors, viruses or hybrids thereof, may be isolated from a variety of sources, genetically engineered, amplified, and/or expressed/generated recombinantly (recombinant polypeptides can be modified or immobilized to arrays in accordance with the invention). Any recombinant expression system can be used, including bacterial, mammalian, yeast, insect or plant cell expression systems.

Alternatively, these nucleic acids can be synthesized in vitro by well-known chemical synthesis techniques, as described in, e.g., Carruthers (1982) Cold Spring Harbor Symp. Quant. Biol. 47:411–418; Adams (1983) J. Am. Chem. Soc. 105:661; Belousov (1997) Nucleic Acids Res. 25:3440–3444; Frenkel (1995) Free Radic. Biol. Med. 19:373–380; Blommers (1994) Biochemistry 33:7886–7896; Narang (1979) Meth. Enzymol. 68:90; Brown (1979) Meth. Enzymol. 68:109; Beaucage (1981) Tetra. Lett. 22:1859; U.S. Pat. No. 4,458,066. Double stranded DNA fragments may then be obtained either by synthesizing the complementary strand and annealing the strands together under appropriate conditions, or by adding the complementary strand using DNA polymerase with a primer sequence.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., Molecular Cloning: a Laboratory Manual (2nd ed.), Vols. 1–3, Cold Spring Harbor Laboratory, (1989); Current Protocols in Molecular Biology, Ausubel, ed. John Wiley & Sons, Inc., New York (1997); Laboratory Techniques in Biochemistry and Molecular Biology: Hybridization With Nucleic Acid Probes, Part I. Theory and Nucleic Acid Preparation, Tijssen, ed. Elsevier, N.Y. (1993).

Another useful means of obtaining and manipulating nucleic acids used in the computer program products, systems and methods of the invention is to clone from genomic samples, and, if necessary, screen and re-clone inserts isolated (or amplified) from, e.g., genomic clones or cDNA clones or other sources of complete genomic DNA. Sources of nucleic acid used to practice the invention (e.g., nucleic acids immobilized to arrays, samples comprising nucleic acids) include genomic or cDNA libraries contained in, or comprised entirely of, e.g., mammalian artificial chromosomes (see, e.g., Ascenzioni (1997) Cancer Lett. 118:135–142; U.S. Pat. Nos. 5,721,118; 6,025,155) (including human artificial chromosomes, see, e.g., Warburton (1997) Nature 386:553–555; Roush (1997) Science 276:38–39; Rosenfeld (1997) Nat. Genet. 15:333–335); yeast artificial chromosomes (YAC); bacterial artificial chromosomes (BAC); P1 artificial chromosomes (see, e.g., Woon (1998) Genomics 50:306–316; Boren (1996) Genome Res. 6:1123–1130); PACs (a bacteriophage P1-derived vector, see, e.g., Ioannou (1994) Nature Genet. 6:84–89; Reid (1997) Genomics 43:366–375; Nothwang (1997) Genomics 41:370–378; Kern (1997) Biotechniques 23:120–124); cosmids, plasmids or cDNAs. The nucleic acids can be deposited as "spots" or "clusters" or "biosites" on substrate surfaces using any protocol, see, e.g., the U.S. Patents cited herein. Labels can be incorporated into nucleic acids by any method or protocol, for example, labeled nucleosides can be incorporated into a nucleic acid by, e.g., nick translation, random primer extension, amplification with degenerate primers (by, e.g., PCR), and the like. The sample nucleic acids or the immobilized nucleic acids can be labeled.

Amplification of Nucleic Acids

Amplification using oligonucleotide primers can be used to generate nucleic acids used in the compositions and methods of the invention, to detect or measure levels of test or control samples hybridized to an array, and the like. The skilled artisan can select and design suitable oligonucleotide amplification primers. Amplification methods are also well known in the art, and include, e.g., polymerase chain reaction, PCR (PCR PROTOCOLS, A GUIDE TO METHODS AND APPLICATIONS, ed. Innis, Academic Press, N.Y. (1990) and PCR STRATEGIES (1995), ed. Innis, Academic Press, Inc., N.Y., ligase chain reaction (LCR) (see, e.g., Wu (1989) Genomics 4:560; Landegren (1988) Science 241:1077; Barringer (1990) Gene 89:117); transcription amplification (see, e.g., Kwoh (1989) Proc. Natl. Acad. Sci. USA 86:1173); and, self-sustained sequence replication (see, e.g., Guatelli (1990) Proc. Natl. Acad. Sci. USA 87:1874); Q Beta replicase amplification (see, e.g., Smith (1997) J. Clin. Microbiol. 35:1477–1491), automated Q-beta replicase amplification assay (see, e.g., Burg (1996) Mol. Cell. Probes 10:257–271) and other RNA polymerase mediated techniques (e.g., NASBA, Cangene, Mississauga, Ontario); see also Berger (1987) Methods Enzymol. 152:307–316; Sambrook; Ausubel; U.S. Pat. Nos. 4,683,195 and 4,683,202; Sooknanan (1995) Biotechnology 13:563–564.

Hybridizing Nucleic Acids

In practicing the methods of the invention and using the compositions (e.g., computer program products) of the invention, test and control samples of nucleic acid are hybridized to immobilized probe nucleic acid, e.g., on arrays. In alternative aspects, the hybridization and/or wash conditions are carried out under moderate conditions, stringent conditions and very stringent conditions. An extensive guide to the hybridization of nucleic acids is found in, e.g., Sambrook Ausubel, Tijssen. Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe. An example of stringent hybridization conditions for hybridization of complementary nucleic acids which have more than 100 complementary residues on an array or a filter in a Southern or northern blot is 42° C. using standard hybridization solutions (see, e.g., Sambrook), with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, e.g., Sambrook). Often, a high stringency wash is preceded by a medium or low stringency wash to remove background probe signal. An example medium stringency wash for a duplex of, e.g., more than 100 nucleotides, is 1×SSC at 45° C. for 15 minutes. An example of a low stringency wash for a duplex of, e.g., more than 100 nucleotides, is 4× to 6×SSC at 40° C. for 15 minutes.

In alternative aspects of the compositions and methods of the invention, e.g., in practicing comparative nucleic acid hybridization, such as comparative genomic hybridization (CGH) with arrays, the fluorescent dyes Cy3™ and Cy5™ are used to differentially label nucleic acid fragments from two samples, e.g., the array-immobilized nucleic acid versus the sample nucleic acid, or, nucleic acid generated from a control versus a test cell or tissue. Many commercial instruments are designed to accommodate to detection of these two dyes. To increase the stability of Cy5™, or fluors or other oxidation-sensitive compounds, antioxidants and free radical scavengers can be used in hybridization mixes, the hybridization and/or the wash solutions. Thus, Cy5™ signals are dramatically increased and longer hybridization times are possible. See WO 0194630 A2 and U.S. Patent Application No. 20020006622.

To further increase the hybridization sensitivity, hybridization can be carried out in a controlled, unsaturated humidity environment; thus, hybridization efficiency is significantly improved if the humidity is not saturated. See WO 0194630 A2 and U.S. Patent Application No. 20020006622. The hybridization efficiency can be improved if the humidity is dynamically controlled, i.e., if the humidity changes during hybridization. Mass transfer will be facilitated in a dynamically balanced humidity environment. The humidity in the hybridization environment can be adjusted stepwise or continuously. Array devices comprising housings and controls that allow the operator to control the humidity during pre-hybridization, hybridization, wash and/or detection stages can be used. The device can have detection, control and memory components to allow pre-programming of the humidity (and temperature (see below), and other parameters) during the entire procedural cycle, including pre-hybridization, hybridization, wash and detection steps. See WO 0194630 A2 and U.S. Patent Application No. 20020006622.

The methods of the invention can incorporate hybridization conditions comprising temperature fluctuation. Hybridization has much better efficiency in a changing temperature environment as compared to conditions where the temperature is set precisely or at relatively constant level (e.g., plus or minus a couple of degrees, as with most commercial ovens). Reaction chamber temperatures can be fluctuatingly modified by, e.g., an oven, or other device capable of creating changing temperatures. See WO 0194630 A2 and U.S. Patent Application No. 20020006622.

The methods of the invention can comprise hybridization conditions comprising osmotic fluctuation. Hybridization efficiency (i.e., time to equilibrium) can also be enhanced by a hybridization environment that comprises changing hyper-/hypo-tonicity, e.g., a solute gradient. A solute gradient is created in the device. For example, a low salt hybridization solution is placed on one side of the array hybridization chamber and a higher salt buffer is placed on the other side to generate a solute gradient in the chamber. See WO 0194630 A2 and U.S. Patent Application No. 20020006622.

Blocking the Ability of Repetitive Nucleic Acid Sequences to Hybridize

The methods of the invention can comprise a step of blocking the ability of repetitive nucleic acid sequences to hybridize (i.e., blocking "hybridization capacity") in the immobilized nucleic acid segments. The hybridization capacity of repetitive nucleic acid sequences in the sample nucleic acid sequences can be blocked by mixing sample nucleic acid sequences with unlabeled or alternatively labeled repetitive nucleic acid sequences. Sample nucleic acid sequences can be mixed with repetitive nucleic acid sequences before the step comprising contacting with the array-immobilized nucleic acid segments. The repetitive nucleic acid sequences can be unlabeled.

In one aspect, the repetitive nucleic acid sequences are blocked using Cot-1 DNA or equivalent. Repetitive sequences from the heterochromatin regions constitute a major component of Cot-1 DNA. See, e.g., Wang (1995) Jpn. J. Hum. Genet. 40:243–252. In another aspect, salmon sperm DNA can be used to block repetitive nucleic acid sequences. See, e.g., U.S. Pat. Nos. 6,342,354; 6,333,177. In another aspect, SST sequences or equivalent are used to block repetitive sequences. SST sequences are repetitive sequences in a genome identified by a fast Sensitive Search Tool (SST). SSTs are determined by a Repeat Pattern Toolkit (RPT) that consists of tools for analyzing repetitive sequences in a genome. RPT takes as input a single sequence in GenBank format and finds both coding (possible gene duplications, pseudogenes, homologous genes) and non-coding repeats. RPT locates all repeats using the fast Sensitive Search Tool (SST). These repeats are evaluated for statistical significance utilizing a sensitive All-PAM search and their evolutionary distance is estimated. The repeats are classified into families of similar sequences. RPT can be found, e.g., at the Institute for Biomedical Computing at Washington University in St. Louis. See also, e.g., Agarwal (1994) Proc. Int. Conf. Intell. Syst. Mol. Biol. 2:1–9; Ting (1995) DNA Cell. Biol. 14:83–85. SST sequences, salmon sperm and Cot-1 sequences and/or various combinations thereof also can be used to block repetitive sequences.

A number of methods for removing and/or disabling the hybridization capacity of repetitive sequences using, e.g., Cot-1 and/or SST, are known; see, e.g., Craig (1997) Hum. Genet. 100:472–476; WO 93/18186. Repetitive DNA sequences can be removed from library probes by means of magnetic purification and affinity PCR, see, e.g., Rauch (2000) J. Biochem. Biophys. Methods 44:59–72.

Polypeptides

The invention is also directed to arrays comprising labeled immobilized polypeptides, peptides and peptidomimetics and analogs thereof (including small molecules). The polypeptides, peptides and peptidomimetics can be immobilized to a substrate surface using any methodology, including covalent or non-covalent, direct or indirect, attachment to a surface.

For example, a polypeptide (or a nucleic acid, lipid or polysaccharide) can be modified by reaction with a compound having the formula: R1—X—R2, where R1 is a cyclic ether group or an amino group, R2 is an alkoxysilane group and X is a moiety chemically suitable for linking the cyclic ether group or the amino group to the alkoxysilane group. As noted above, the terms "polypeptide," "protein," and "peptide," used to practice the invention, include compositions of the invention that also include "analogs," or "conservative variants" and "mimetics" or "peptidomimetics." The terms "mimetic" and "peptidomimetic" refer to a synthetic chemical compounds. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetics' structure and/or activity. Polypeptide mimetic compositions can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., to induce or stabilize a secondary structure, e.g., a beta turn, gamma turn, beta sheet, alpha helix conformation, and the like. A polypeptide can be characterized as a mimetic when all or some of its residues are joined by chemical means other than natural peptide bonds. Individual peptidomimetic residues can be joined by peptide bonds, other chemical bonds or coupling means, such as, e.g., glutaraldehyde, N-hydroxysuccinimide esters, bifunctional maleimides, N,N'-dicyclohexylcarbodiimide (DCC) or N,N'-diisopropylcarbodiimide (DIC). Linking groups that can be an alternative to the traditional amide bond ("peptide bond") linkages include, e.g., ketomethylene (e.g., —C(=O)—CH2— for —C(=O)—NH—), aminomethylene (CH2—NH), ethylene, olefin (CH=CH), ether (CH2—O), thioether (CH2—S), tetrazole (CN4—), thiazole, retroamide, thioamide, or ester (see, e.g., Spatola (1983) in Chemistry and Biochemistry of Amino Acids, Peptides and Proteins, Vol. 7, pp 267–357, "Peptide Backbone Modifications," Marcell Dekker, NY). A polypeptide can also be characterized as a mimetic by containing all or some non-natural residues in place of naturally occurring amino acid residues; non-natural residues are well described in the scientific and patent literature. The skilled artisan will recognize that individual synthetic residues and polypeptides incorporating mimetics can be synthesized using a variety of procedures and methodologies, which are well described in the scientific and patent literature, e.g., Organic Syntheses Collective Volumes, Gilman, et al., supra. Polypeptides incorporating mimetics can also be made using solid phase synthetic procedures, as described, e.g., by U.S. Pat. No. 5,422,426. Peptides and peptide mimetics can also be synthesized using combinatorial methodologies. Various techniques for generation of peptide and peptidomimetic libraries are well known, and include, e.g., multipin, tea bag, and split-couple-mix techniques; see, e.g., al-Obeidi (1998) Mol. Biotechnol. 9:205–223; Hruby (1997) Curr. Opin. Chem. Biol. 1:114–119; Ostergaard (1997) Mol. Divers. 3:17–27; Ostresh (1996) Methods Enzymol. 267:220–234. Modified polypeptide and peptides can be further produced by chemical modification methods, see, e.g., Belousov (1997) Nucleic Acids Res. 25:3440–3444; Frenkel (1995) Free Radic. Biol. Med. 19:373–380; Blommers (1994) Biochemistry 33:7886–7896. These peptides can also be synthesized, whole or in part, using chemical methods well known in the art (see e.g., Caruthers (1980) Nucleic Acids Res. Symp. Ser. 215–223; Horn (1980) Nucleic Acids Res. Symp. Ser. 225–232; Banga, A. K., Therapeutic Peptides and Proteins, Formulation, Processing and Delivery Systems (1995) Technomic Publishing Co., Lancaster, Pa. Peptide synthesis can be performed using various solid-phase techniques (see e.g., Roberge (1995) Science 269:202; Merrifield (1997) Methods Enzymol. 289:3–13) and automated synthesis may be used. See also, U.S. Pat. Nos. 6,245,886; 6,169,073; 6,034,211.

Arrays, or "BioChips"

The invention provides computer program products, systems and methods using "arrays" or "microarrays" or "biochips" or "chips." The arrays comprise a plurality of biological molecules, e.g., nucleic acid segments, wherein each biological molecule is immobilized to a discrete and known spot on a substrate surface to form an array of biological molecules.

Arrays are generically a plurality of target elements immobilized onto the surface of the array as defined "spots" or "clusters," or "biosites," each target element comprising a one or more biological molecules (e.g., nucleic acids or polypeptides) immobilized to a solid surface for specific binding (e.g., hybridization) to a molecule in a sample. The immobilized nucleic acids can contain sequences from specific messages (e.g., as cDNA libraries) or genes (e.g., genomic libraries), including a human genome. Other target elements can contain reference sequences and the like. The biological molecules of the arrays may be arranged on the solid surface at different sizes and different densities. The densities of the biological molecules in a cluster and the number of clusters on the array will depend upon a number of factors, such as the nature of the label, the solid support, the degree of hydrophobicity of the substrate surface, and the like. Each cluster/biosite may comprise substantially the same biological molecule (e.g., nucleic acid), or, a mixture of biological molecules (e.g., nucleic acids of different lengths and/or sequences). Thus, for example, a cluster/biosite may contain more than one copy of a cloned piece of DNA, and each copy may be broken into fragments of different lengths.

Array substrate surfaces onto which biological molecules (e.g., nucleic acids) are immobilized can include nitrocellulose, glass, quartz, fused silica, plastics and the like, as discussed further, below. The compositions and methods of the invention can incorporate in whole or in part designs of arrays, and associated components and methods, as described, e.g., in U.S. Pat. Nos. 6,344,316; 6,197,503; 6,174,684; 6,159,685; 6,156,501; 6,093,370; 6,087,112; 6,087,103; 6,087,102; 6,083,697; 6,080,585; 6,054,270; 6,048,695; 6,045,996; 6,022,963; 6,013,440; 5,959,098; 5,856,174; 5,843,655; 5,837,832; 5,770,456; 5,723,320; 5,700,637; 5,695,940; 5,556,752; 5,143,854; see also, e.g., WO 99/51773; WO 99/09217; WO 97/46313; WO 96/17958; WO 89/10977; see also, e.g., Johnston (1998) Curr. Biol. 8:R171–174; Schummer (1997) Biotechniques 23:1087–1092; Kern (1997) Biotechniques 23:120–124; Solinas-Toldo (1997) Genes, Chromosomes & Cancer 20:399–407; Bowtell (1999) Nature Genetics Supp. 21:25–32; Epstein (2000) Current Opinion in Biotech. 11:36–41; Mendoza (1999 Biotechniques 27: 778–788; Lueking (1999) Anal. Biochem. 270:103–111; Davies (1999) Biotechniques 27:1258–1261.

Substrate Surfaces

Substrate surfaces that can be used in the compositions and methods of the invention include, for example, glass (see, e.g., U.S. Pat. No. 5,843,767), ceramics, quartz. The arrays can have substrate surfaces of a rigid, semi-rigid or flexible material. The substrate surface can be flat or planar, be shaped as wells, raised regions, etched trenches, pores, beads, filaments, or the like. Substrate surfaces can also comprise various materials such as paper, crystalline substrates (e.g. gallium arsenide), metals, metalloids, polacryloylmorpholide, various plastics and plastic copolymers, Nylon™, Teflon™, polyethylene, polypropylene, poly(4-methylbutene), polystyrene, polystyrene/ latex, polymethacrylate, poly(ethylene terephthalate), rayon, nylon, poly(vinyl butyrate), polyvinylidene difluoride (PVDF) (see, e.g., U.S. Pat. No. 6,024,872), silicones (see, e.g., U.S. Pat. No. 6,096,817), polyformaldehyde (see, e.g., U.S. Pat. Nos. 4,355,153; 4,652,613), cellulose (see, e.g., U.S. Pat. No. 5,068,269), cellulose acetate (see, e.g., U.S. Pat. No. 6,048,457), nitrocellulose, various membranes and gels (e.g., silica aerogels, see, e.g., U.S. Pat. No. 5,795,557), paramagnetic or superparamagnetic microparticles (see, e.g., U.S. Pat. No. 5,939,261) and the like. Silane (e.g., mono- and dihydroxyalkylsilanes, aminoalkyltrialkoxysilanes, 3-aminopropyl-triethoxysilane, 3-aminopropyltrimethoxysilane) can provide a hydroxyl functional group for reaction with an amine functional group.

Arrays Comprising Calibration Sequences

The invention provides novel arrays comprising immobilized calibration sequences for normalizing the results of array-based hybridization reactions, and methods for using these calibration sequences, e.g., to determine the copy number of a calibration sequence to "normalize" or "calibrate" ratio profiles. The calibration sequences can be substantially the same as a unique sequence in an immobilized nucleic acid sequence on an array. For example, a "marker" sequence from each "spot" or "biosite" on an array (which is present only on that spot, making it a "marker" for that spot) is represented by a corresponding sequence on one or more "control" or "calibration" spot(s).

Alternatively, for biological molecules other than nucleic acids, e.g., polypeptides, lipids, polysaccharides, small molecules, the invention provides novel arrays comprising immobilized calibration molecules for normalizing the results of array-based binding reactions, and methods for using these calibration sequences The "control spots" or "calibration spots" are used for "normalization" to provide information that is reliable and repeatable. Control spots can provide a consistent result independent of the labeled sample hybridized to the array (or a labeled binding molecule from a sample). The control spots can be used to generate a "normalization" or "calibration" curve to offset possible intensity errors between the two arrays (or more) used in the in silico, array-based methods of the invention.

One method of generating a control on the array would be to use an equimolar mixture of all the biological molecules (e.g., nucleic acid sequences) spotted on the array and generating a single spot. This single spot would have equal amounts of the biological molecules (e.g., nucleic acid sequences) from all the other spots on the array. Multiple control spots can be generated by varying the concentration of the equimolar mixture. For example, in one aspect, the invention provides arrays comprising at least one "calibration spot" or "calibration biosite" comprising a plurality of biological molecules (e.g., nucleic acid sequences) comprising at least one molecules or sequence from each spot on the array. In one aspect, the biological molecule/sequence from each "test" spot on the array that is also part of the "calibration spot" is unique to that particular "test" spot in that it is not present on any of the other "test spots." In other words, the sequence is a "marker" for that spot. For example, in one aspect, an array of the invention has 100 spots, each spot having sample nucleic acid, e.g., genomic nucleic acid. The 100 spots can represent the sequences of substantially a complete chromosome or a known subset of a chromosome, or an entire genome. These 100 spots can be used as "test spots" for hybridization to sample nucleic acid to determine, e.g., gene copy numbers or for comparative genomic hybridization. A 101st spot, a "calibration spot," has at least one sample of nucleic acid from each of the 100 "test" spots. As noted above, each sample of nucleic acid from each of the 100 "test" spots is a "marker" for that spot. Thus, if the 100 "test spots" represent the entire genome of an organism and the labeled sample applied to the array represents the entire genome of a cell (with a complement of sequences that correspond to the genome immobilized onto the 100 spots of the array), then after hybridization the "calibration spot" should have 100 times the labeling (e.g., fluorescence) intensity than each of the 100 "test spots." In another aspect, the array has a first "calibration spot" having x amount of nucleic acid from each of the 100 "test" spots and at least a sec each of the 100 "test" spots. Thus, using the example above, the second "calibration spot" should have only 50 times the labeling (e.g., fluorescence) intensity than each of the 100 "test spots." The array can further comprise further "calibration spots," each representing a serial dilution of "test spot" nucleic acid. In another aspect, the array comprises an additional "calibration spot" having 2x amount of nucleic acid from each of the 100 "test" spots. Thus, using the example above, the second "calibration spot" should have only 200 times the labeling (e.g., fluorescence) intensity than each of the 100 "test spots."

For example, a hybridization using a labeled sample is performed using an array of the invention. In one aspect, the array has at least one control spot comprising an equimolar mixture of a sufficient number of different nucleic acid sequences present in the sample to be tested. This will result in sufficient hybridization to the control spot independent of a few missing or additional nucleic acid sequences in the labeled sample. Hence, this control spot(s) will behave as a positive control because it will always exhibit a high intensity value. The labeled sample contains a plurality of nucleic acid sequences. Since the control spot has many sequences complementary to sample sequences, many of the labeled sample nucleic acid sequences will bind to the control spot. This will result in the control spot having a higher label (e.g., fluorescence) intensity than most of the other spots on the array which may contain a few or only a single nucleic acid sequence complementary to a labeled sequence in a sample.

For example, in one exemplary aspect, when an array consists of 100 different nucleic acid sequences in the form of 100 different spots (each of the 100 nucleic acids on a different "test spot"), the "control" or "calibration" spot will contain all 100 nucleic acid sequences in a single spot. After hybridization with a labeled sample that contains 2 copies of each of the 100 nucleic acid sequences, one would see that each of the 100 "test" spots would exhibit an intensity of 2x, where x is the intensity of label generated by the presence (stringent hybridization to an array-immobilized nucleic acid) of a single copy of the nucleic acid sequence. The control spot would exhibit an intensity of $(2x)(100)=(200x)$ because the control spot has all the 100 nucleic acid sequences at a fixed concentration.

In another aspect of the invention, the labeled sample applied to an array of the invention is abnormal (in genotype/ phenotype). After hybridization with a labeled sample that contains 2 copies of each of the 100 nucleic acid sequences (immobilized in 100 different "test spots") and an extra copy of one of the 100 sequences, one would see that each of the 100 spots would exhibit an intensity of 2x with the exception of one spot which would exhibit an intensity of 3x, where x is the intensity generated by the presence of a single copy of the nucleic acid sequence. This would also mean that the control spot would exhibit an intensity of $(2x)(99)+(3x)(1)=(201x)$.

The invention provides an in silico, array-based method for determining the relative amount of a biological molecule (e.g., nucleic acid sequence) in two or more samples using two or more arrays. In one aspect, the each of the arrays comprises at least one "control" or "calibration" spot. These control spots can be used to compute a normalization factor and/or to calculate a normalization, or calibration, curve. Because the difference in intensity of labels associated with test and calibration spots after hybridization is so small as compared to noise effectively the control spots should show almost the same intensities, independent of a normal or abnormal labeled sample. However, as noted above, the presence of a single extra copy of a biological molecule, e.g., a single extra copy of a sequence, such as a gene (i.e., a single extra detectable label) can be detected and computed. In one aspect, the arrays of the invention comprise multiple control spots. Thus, concentrations of equimolar mixtures can be titrated to generate a calibration, or normalization, curve that can be used to offset the intensity errors between the two (or more) arrays.

In another aspect, the calibration spot(s) use nucleic acid from genomes other than that spotted on the array. For example, in one aspect, human genomic DNA is used in the "test spots" (for, e.g., human genomic CGH) and the calibration spot(s) are non-human nucleic acid, e.g., the genomic DNA from Mus, Drosophila or equivalent. Thus, some or all of the "test spots" would include at least one "marker" Drosophila (or equivalent) sequence also on a "calibration spot."

Normalizing, or Calibrating, Ratio Profiles

One aspect of the methods and compositions of the invention comprises determining the average copy number of a calibration molecule (e.g., a nucleic acid sequence), wherein a known amount of calibration molecule is mixed with the first and the second samples, and the calibration molecule is known to bind to molecules immobilized on the two or more arrays, e.g., the calibration molecule is substantially the same (can hybridize or bind to) a unique sequence in an immobilized nucleic acid sequence present in both arrays. A known amount of calibration molecule (e.g., sequence) is added to each sample. The expected ratio of the known amount of calibration molecule is detected on the two arrays. Different or the same amounts of calibration molecule can be added. For example, if the CGH ratio should be 1:1, and the detected ratio is 2:1, this figure can be used to normalize the ratio of the amount of label associated with the nucleic acid sequence in the first and the second array. Normalization, or calibration, adjusts the sample ratio by a figure representing the difference between the expected ratio calibration sequence and the detected ratio of calibration sequence on the two arrays.

In one aspect, sequences (e.g., clones) from a genome other than that in one of the sample (e.g., such as Drosophila) are used as a calibration sequence. Thus, there would be no crossover hybridization from the genome being tested. In one aspect, calibration sequences (e.g., clones) are spotted in titrated concentrations on each of the arrays. In each of the labeled samples, a defined amount of the calibration DNA would be included (typically, a small amount). This would result in hybridization of the calibration DNA to the spotted titrations and provide a calibration curve. Use of calibration curves provide more accuracy for normalization across the range of intensities one can expect on an array to show multiple copy changes and ratios.

Detectable Labels and Labeling of Biological Molecules

The methods and compositions of the invention use biological molecules (e.g., nucleic acids) that are associated with a detectable label, e.g., have incorporated or have been conjugated to a detectable moiety. The association with the detectable moiety can be covalent or non-covalent. In another aspect, the array-immobilized biological molecules (e.g., nucleic acids) and test sample biological molecules (e.g., nucleic acids) are differentially detectable, e.g., they emit difference signals.

Useful labels include, e.g., 32P, 35S, 3H, 14C, 125I, 131I; fluorescent dyes (e.g., Cy5™, Cy3™, FITC, rhodamine, lanthanide phosphors, Texas red), electron-dense reagents (e.g. gold), enzymes, e.g., as commonly used in an ELISA (e.g., horseradish peroxidase, beta-galactosidase, luciferase, alkaline phosphatase), colorimetric labels (e.g. colloidal gold), magnetic labels (e.g. Dynabeads™), biotin, dioxigenin, or haptens and proteins for which antisera or monoclonal antibodies are available. In other aspects, fluorescent, bioluminescent and/or chemiluminescent labels are used.

The label can be directly incorporated into the biological molecules (e.g., nucleic acids) or other target compound to be detected, or it can be attached to a probe or antibody that hybridizes or binds to the target. A peptide can be made detectable by incorporating (e.g., into a nucleoside base) predetermined polypeptide epitopes recognized by a secondary reporter (e.g., leucine zipper pair sequences, binding sites for secondary antibodies, transcriptional activator polypeptide, metal binding domains, epitope tags). Label can be attached by spacer arms of various lengths to reduce potential steric hindrance or impact on other useful or desired properties. See, e.g., Mansfield (1995) Mol Cell Probes 9:145–156. In array-based CGH, typically fluors are paired together (one labeling control and another the test nucleic acid), e.g., rhodamine and fluorescein (see, e.g., DeRisi (1996) Nature Genetics 14:458–460), or lissamine-conjugated nucleic acid analogs and fluorescein-conjugated nucleotide analogs (see, e.g., Shalon (1996) supra); or Spectrum Red™ and Spectrum Green™ (Vysis, Downers Grove, Ill.) or Cy3™ and Cy5™ (see below).

Cyanine and related dyes, such as merocyanine, styryl and oxonol dyes, are particularly strongly light-absorbing and highly luminescent, see, e.g., U.S. Pat. Nos. 4,337,063; 4,404,289; 6,048,982. Cy3™ and Cy5™ can be used together; both are fluorescent cyanine dyes produced by Amersham Life Sciences (Arlington Heights, Ill.).

In one aspect, lanthanide metal ions such as lanthanum [La], cerium [Ce], praseodyme [Pr], gadolinium [Gd], dysprosium [Dy], ytterbium [Yb], and lutetium [Lu] are used as detectable labels. Non-lanthanides that can be detected are also used in the methods of the invention and include lead [Pb] and bismuth [Bi]. See, e.g. Krause (1996) Invest. Radiol. 31:502–511.

Detectable moieties can be incorporated into sample nucleic acids and/or array-immobilized nucleic acid by transcription, e.g., by random-primer labeling using Klenow polymerase, or "nick translation," or, amplification, or equivalent. For example, in one aspect, a nucleoside base is conjugated to a detectable moiety, such as a fluorescent dye, e.g., Cy3™ or Cy5™, and then incorporated into a nucleic acid for immobilization onto an array or for use as a sample nucleic acid. Samples of genomic DNA can be incorporated with Cy3™- or Cy5™-dCTP conjugates mixed with unlabeled dCTP. According to manufacturer's instructions, if generating labeled target by PCR, a mixture of 33% modified to 66% unmodified dCTP gives maximal incorporation of label; when modified dCTP made up 50% or greater, the PCR reaction was inhibited. Cy5™ is typically excited by the 633 nm line of HeNe laser, and emission is collected at 680 nm. See also, e.g., Bartosiewicz (2000) Archives of Biochem. Biophysics 376:66–73; Schena (1996) Proc. Natl. Acad. Sci. USA 93:10614–10619; Pinkel (1998) Nature Genetics 20:207–211; Pollack (1999) Nature Genetics 23:41–46.

In another aspect, when using PCR or nick translation to label nucleic acids, modified nucleotides synthesized by coupling allylamine-dUTP to the succinimidyl-ester derivatives of the fluorescent dyes or haptenes (such as biotin or digoxigenin) are used; this method allows custom preparation of most common fluorescent nucleotides, see, e.g., Henegariu (2000) Nat. Biotechnol. 18:345–348. Other fluorescent nucleotide analogs can be used, see, e.g., Jameson (1997) Methods Enzymol. 278:363–390; Zhu (1994) Nucleic Acids Res. 22:3418–3422. U.S. Pat. Nos. 5,652,099 and 6,268,132 also describe nucleoside analogs for incorporation into nucleic acids, e.g., DNA and/or RNA, or oligonucleotides, via either enzymatic or chemical synthesis to produce fluorescent oligonucleotides. U.S. Pat. No. 5,135,717 describes phthalocyanine and tetrabenztriazaporphyrin reagents for use as fluorescent labels.

In the compositions and methods of the invention, labeling with a detectable composition (labeling with a detectable moiety) also can include a nucleic acid attached to another biological molecule, such as a nucleic acid, e.g., a nucleic acid in the form of a stem-loop structure as a "molecular beacon" or an "aptamer beacon." Molecular beacons as detectable moieties are well known in the art; for example, Sokol (1998) Proc. Natl. Acad. Sci. USA 95:11538–11543, synthesized "molecular beacon" reporter oligodeoxynucleotides with matched fluorescent donor and acceptor chromophores on their 5' and 3' ends. In the absence of a complementary nucleic acid strand, the molecular beacon remains in a stem-loop conformation where fluorescence resonance energy transfer prevents signal emission. On hybridization with a complementary sequence, the stem-loop structure opens increasing the physical distance between the donor and acceptor moieties thereby reducing fluorescence resonance energy transfer and allowing a detectable signal to be emitted when the beacon is excited by light of the appropriate wavelength. See also, e.g., Antony (2001) Biochemistry 40:9387–9395, describing a molecular beacon comprised of a G-rich 18-mer triplex forming oligodeoxyribonucleotide. See also U.S. Pat. Nos. 6,277,581 and 6,235,504.

Aptamer beacons are similar to molecular beacons; see, e.g., Hamaguchi (2001) Anal. Biochem. 294:126–131; Poddar (2001) Mol. Cell. Probes 15:161–167; Kaboev (2000) Nucleic Acids Res. 28:E94. Aptamer beacons can adopt two or more conformations, one of which allows ligand binding. A fluorescence-quenching pair is used to report changes in conformation induced by ligand binding. See also, e.g., Yamamoto (2000) Genes Cells 5:389–396; Smirnov (2000) Biochemistry 39:1462–1468.

In addition to methods for labeling molecules (e.g., nucleic acids) with fluorescent dyes, methods for the simultaneous detection of multiple fluorophores are well known in the art, see, e.g., U.S. Pat. Nos. 5,539,517; 6,049,380; 6,054,279; 6,055,325. For example a spectrograph can image an emission spectrum onto a two-dimensional array of light detectors; a full spectrally resolved image of the array is thus obtained. Photophysics of the fluorophore, e.g., fluorescence quantum yield and photodestruction yield, and the sensitivity of the detector are read time parameters for an oligonucleotide array. With sufficient laser power and use of Cy5™ and/or Cy3™, which have lower photodestruction yields an array can be read in less than 5 seconds.

When using two or more fluors together (e.g., as in a CGH), such as Cy3™ and Cy5™, it is necessary to create a composite image of all the fluors. To acquire the two or more images, the array can be scanned either simultaneously or sequentially. Charge-coupled devices, or CCDs, are used in microarray scanning systems, including the multiplexed systems of the invention. Thus, CCDs used in the systems and methods of the invention can scan and analyze multicolor fluorescence images; see, e.g., U.S. Patent Application Nos. 6,261,776; 6,252,664; 6,191,425; 6,143,495; 6,140,044; 6,066,459; 5,943,129; 5,922,617; 5,880,473; 5,846,708; 5,790,727; and, the patents cited in the discussion of arrays, herein. See also, e.g., Bornfleth (1996) Cytometry 24:1–13.

The invention further comprises data analysis, which can include the steps of determining, e.g., fluorescent intensity as a function of substrate position, removing "outliers" (data deviating from a predetermined statistical distribution), or calculating the relative binding affinity of the targets from the remaining data. The resulting data can be displayed as an image with color in each region varying according to the light emission or binding affinity between targets and probes. See, e.g., U.S. Pat. Nos. 5,324,633; 5,830,645; 5,863,504; 6,045,996; 6,159,685. The invention can also incorporate a device for detecting a labeled marker on a sample located on a support, see, e.g., U.S. Pat. No. 5,578,832.

Fragmentation and Digestion of Nucleic Acid

In practicing the methods and compositions of the invention, immobilized and sample nucleic acids can be in a variety of lengths. For example, in one aspect, genomic nucleic acids are labeled fragments consisting of a length smaller than about 200 bases. Use of labeled genomic DNA limited to this small size significantly improves the resolution of the molecular profile analysis, e.g., in array-based CGH. For example, use of such small fragments allows for significant suppression of repetitive sequences and other unwanted, "background" cross-hybridization on the immobilized nucleic acid. Suppression of repetitive sequence hybridization greatly increases the reliability of the detection of copy number differences (e.g., amplifications or deletions) or detection of unique sequences. See WO 0194630 A2 and U.S. patent Application No. 20020006622.

The resultant fragment lengths can be modified by, e.g., treatment with DNase. Adjusting the ratio of DNase to DNA polymerase in a nick translation reaction changes the length of the digestion product. Standard nick translation kits typically generate 300 to 600 base pair fragments. If desired, the labeled nucleic acid can be further fragmented to segments below 200 bases, down to as low as about 25 to 30 bases, random enzymatic digestion of the DNA is carried out, using, e.g., a DNA endonucleases, e.g., DNase (see, e.g., Herrera (1994) J. Mol. Biol. 236:405–411; Suck (1994) J. Mol. Recognit. 7:65–70), or, the two-base restriction endonuclease CviJI (see, e.g., Fitzgerald (1992) Nucleic Acids Res. 20:3753–3762) and standard protocols, see, e.g., Sambrook, Ausubel, with or without other fragmentation procedures.

Other procedures can also be used to fragment genomic DNA, e.g. mechanical shearing, sonication (see, e.g., Deininger (1983) Anal. Biochem. 129:216–223), and the like (see, e.g., Sambrook, Ausubel, Tijssen). For example, one mechanical technique is based on point-sink hydrodynamics that result when a DNA sample is forced through a small hole by a syringe pump, see, e.g., Thorstenson (1998) Genome Res. 8:848–855. See also, Oefner (1996) Nucleic Acids Res. 24:3879–3886; Ordahl (1976) Nucleic Acids Res. 3:2985–2999. Fragment size can be evaluated by a variety of techniques, including, e.g., sizing electrophoresis, as by Siles (1997) J. Chromatogr. A. 771:319–329, that analyzed DNA fragmentation using a dynamic size-sieving polymer solution in a capillary electrophoresis. Fragment sizes can also be determined by, e.g., matrix-assisted laser desorption/ionization time-of-flight mass spectrometry, see, e.g., Chiu (2000) Nucleic Acids Res. 28:E31.

Generating Molecular Profiles of Sample Nucleic Acids

The invention provides compositions and methods for generating molecular profiles of nucleic acid samples, such as samples of genomic DNA or a cDNA library. In one aspect, array-bound nucleic acids are contacted with a sample comprising nucleic acids; the binding of the sample nucleic acids to the array is detected to generate a molecular profile of the sample nucleic acid. In alternative aspects, the molecular profile can be a comparative genomic hybridization (CGH) reaction; detection of a genomic DNA amplification, a genomic DNA deletion, or a genomic DNA insertion; detection of a point mutation, such as identification of a single-nucleotide polymorphism (SNP); differential methylation hybridization (DMH), where the array-bound nucleic acids are CpG island tags; detection of transcriptionally active regions of a genome (using, e.g., nuclear run-off assays); analysis of a chromatin structure; and analysis of a telomeric structure (such as telomeric erosion or telomeric addition). All of these procedures are well known in the art, and any molecular biology procedure or analysis, can be performed using the modified biological molecules or arrays of the invention.

Comparative Genomic Hybridization (CGH)

The compositions and methods of the invention provide in silico comparative genomic hybridization (CGH) reactions. Thus, in one aspect, labeled genomic nucleic acid is immobilized onto substrate surfaces. CGH is a molecular cytogenetics approach that can be used to detect regions in a genome undergoing quantitative changes, i.e. gains or losses of copy numbers. Analysis of genomes of tumor cells can detect a region or regions of anomaly under going gains and/or losses. Differential expression of hundreds of genes can be analyzed using a cDNA array, thus facilitating characterization of gene expression in normal and diseased tissues. Generating a molecular profile of a nucleic acid sample by comparative genomic hybridization using the invention can be practiced with methods and compositions known in the art, see, e.g., U.S. Pat. Nos. 6,197,501; 6,159,685; 5,976,790; 5,965,362; 5,856,097; 5,830,645; 5,721,098; 5,665,549; 5,635,351; U.S. Patent Application Nos. 20010018183; 20020028460 and 20020006623; and, Diago (2001) American J. of Pathol. May;158(5) :1623–1631; Theillet (2001) Bull. Cancer 88:261–268; Werner (2001) Pharmacogenomics 2:25–36; Jain (2000) Pharmacogenomics 1:289–307.

Detection of Single-Nucleotide Polymorphisms (SNPs)

In one aspect, the compositions and methods of the invention are used to detect point mutations, such as single-nucleotide polymorphisms (SNPs). Thus, in one aspect, labeled nucleic acid for detecting SNPs is immobilized onto substrate surfaces. Arrays can be used for high-throughput genotyping approaches for pharmacogenomics, where numerous individuals are studied with thousands of SNP markers. Generating a molecular profile of a nucleic acid sample by the analysis and detection of SNPs using the invention can be practiced with methods and compositions known in the art, see, e.g., U.S. Pat. Nos. 6,221,592; 6,110,709; 6,074,831; 6,015,888; and, Kwok (2000) Pharmacogenomics 1:95–100; Riley (2000) Pharmacogenomics 1:39–47; Kokoris (2000) Mol. Diagn. 5:329–340; Shi (2001) Clin. Chem. 47:164–172; Fan (2000) Genome Res. 10:853–860; Ianonne (2000) Cytometry 39:131–140; Cai (2000) Genomics.66:135–143; Chen (2000) Genome Res. 10:549–557; Syvanen (1999) Hum. Mutat. 13:1–10; Pastinen (1997) Genome Res. 7:606–614.

Differential Methylation Hybridization (DMH)

The compositions and methods of the invention are used in differential methylation hybridization (DMH), including, for example, CpG island analysis. Thus, in one aspect, array-bound labeled nucleic acids comprise CpG island tags. Thus, the invention is used to identify, analyze and map hypermethylated or hypomethylated regions of the genome. In one aspect, the sample nucleic acids can comprise genomic DNA digested with at least one methylation-sensitive restriction endonuclease and the molecular profile comprises detection and mapping of hypermethylated (or hypomethylated) regions of the genome. Any methylation-sensitive restriction endonuclease or equivalent endonuclease enzyme can be used, including, for example, NotI, SmaI, SacII, EagI, MspI, HpaII, Sau3AI and BssHII. In one aspect, both a methylation-sensitive enzyme and its methylation insensitive isoschizomer is used; see, e.g., Robinson (2000) Chromosome Res. 8:635–643; described use of the methylation-sensitive enzyme HpaII and its methylation insensitive isoschizomer MspI. Windhofer (2000) Curr. Genet. 37:194–199, described digestion of genomic DNA with the methylation-sensitive endonuclease Sau3AI and the methylation-insensitive endonuclease NdeII. See also, e.g., Muller (2001) J. Biol. Chem. 276:14271–14278; Memisoglu (2000) J. Bacteriol. 182:2104–2112; Roth (2000) Biol. Chem. 381:269–272. Generating a molecular profile of a nucleic acid sample by the analysis of differential methylation and CpG islands can be practiced with methods and compositions known in the art, see, also, U.S. Pat. Nos. 6,214,556; 6,180,344; 5,851,762; and, WO0127317, WO9928498; WO0044934; and WO1999DE03747 19991119.

Analysis of Telomeric Structure

The compositions and methods of the invention are used in the analysis of telomeric structures, such as telomeric erosion or telomeric addition. Thus, in one aspect, labeled nucleic acid comprising telomeric structures, or, labeled telomeric structures alone, are immobilized onto substrate surfaces. Telomerase assays are useful for cancer detection and diagnosis (see, e.g., Hahn (2001) Ann Med 33:123–129; Meyerson (2000) J. Clin. Oncol. 18:2626–2634; Meyerson (1998) Toxicol. Lett. 102–103:41–5). Using the array-based telomeric structures will accelerate understanding of telomerase biology and lead to clinically relevant telomerase-based therapies. Generating a molecular profile of a nucleic acid sample by the analysis of telomeric structures can be practiced with methods and compositions known in the art, see, e.g., U.S. Pat. Nos. 6,221,590; 6,221,584; 6,022,709; 6,007,989; 6,004,939; 5,972,605; 5,871,926; 5,834,193; 5,830,644; 5,695,932; 5,645,986.

Analysis of Chromatin Structure

The compositions and methods of the invention are used in the analysis of chromatin structure, including chromatin condensation, chromatin decondensation, histone phosphorylation, histone acylation, and the like (see, e.g., Guo (2000) Cancer Res. 60:5667–5672; Mahlknecht (2000) Mol. Med. 6:623–644). Thus, in one aspect, labeled nucleic acid comprising chromatin structures, or, labeled chromatin structures alone, are immobilized onto substrate surfaces. Chromatin structure remodeling occurs in certain cancers (see, e.g., Giamarchi (2000) Adv. Exp. Med. Biol. 480:155–161). Chromatin structure affects nuclear processes that utilize DNA as a substrate, e.g., transcription, replication, DNA repair, and DNA organization within the nucleus. Chromatin structure analysis is useful in fertility assessment; for example, sperm with decondensed chromatin are infertile. DNA damage in patients with untreated cancer can be measured using a sperm chromatin structure assay (see, e.g., Kobayashi (2001) Fertil. Steril. 75:469–475). Generating a molecular profile of a nucleic acid sample by the analysis of chromatin structure can be practiced with methods and compositions known in the art, see, e.g., U.S. Pat. Nos. 6,204,064; 6,187,749; 6,097,485; 5,972,608; 5,919,621; 5,470,709; and, Dreyer (2000) Anal. Cell Pathol. 20:141–150; Hong (2001) Acta Cytol. 45:163–168; Evenson (1991) Reprod. Toxicol. 5:115–125.

EXAMPLES

The following example is offered to illustrate, but not to limit the claimed invention.

Example 1

Making Nucleic Acid Arrays

The following example demonstrates exemplary protocol for making an array used to practice the invention.

Making BAC Microarrays:

BAC clones greater than fifty kilobases (50 kb), and up to about 300 kb, are grown up in Terrific Broth medium. Larger inserts, e.g., clones >300 kb, and smaller inserts, about 1 to 20 kb, are also be used. DNA is prepared by a modified alkaline lysis protocol (see, e.g., Sambrook). The DNA is labeled, as described below.

The DNA is then chemically modified as described by U.S. Pat. No. 6,048,695. The modified DNA is then dissolved in proper buffer and printed directly on clean glass surfaces as described by U.S. Pat. No. 6,048,695. Usually multiple spots are printed for each clone.

Nucleic Acid Labeling and DNase Enzyme Fragmentation:

A standard random priming method is used to label genomic DNA before its attachment to the array, see, e.g., Sambrook. Sample nucleic acid is also similarly labeled. Cy3™ or Cy5™ labeled nucleotides are supplemented together with corresponding unlabeled nucleotides at a molar ratio ranging from 0.0 to about 6 (unlabeled nucleotide to labeled nucleotides). Labeling is carried out at 37° C. for 2 to 10 hours. After labeling the reaction mix is heated up to 95° C. to 100° C. for 3 to 5 minutes to inactivate the polymerase and denature the newly generated, labeled "probe" nucleic acid from the template.

The heated sample is then chilled on ice for 5 minutes. "Calibrated" DNase (DNA endonuclease) enzyme is added to fragment the labeled template (generated by random priming). "Trace" amounts of DNase is added (final concentration was 0.2 to 2 ng/ml; incubation time 15 to 30 minutes) to digest/ fragment the labeled nucleic acid to segments of about 30 to about 100 bases in size.

A number of embodiments of the invention have been described. Nevertheless, it will be understood that various modifications may be made without departing from the spirit and scope of the invention. Accordingly, other embodiments are within the scope of the following claims.

What is claimed is:

1. An array-based method for determining a relative amount of a nucleic acid sequence in two or more samples, the method comprising:

(a) contacting a first sample and a second sample with a first array and a second array respectively, the first and second array comprising a plurality of nucleic acid segments, wherein each nucleic acid segment is immobilized to a discrete and known spot on each of a first substrate surface and a second substrate surface to form the first and the second arrays of nucleic acid segments wherein each said spot comprises a nucleic acid sequence that is a marker for each said spot on the array providing a plurality of markers on the array and the nucleic acid segments immobilized on the second array comprise substantially the same plurality of nucleic acid segments immobilized on the first array, each array further comprising at least one calibration spot comprising a mixture of the same plurality of nucleic acid sequence markers present in all of the other spots of the array, the first sample and second sample each comprising a plurality of nucleic acid segments comprising a detectable label wherein contacting is performed under conditions wherein the labeled nucleic acid segments specifically bind to the nucleic acid segment immobilized on the arrays;

(b) identifying which spots on the first and the second arrays are specifically bound to a labeled nucleic acid segment and measuring the an amount of label on each spot;

(c) comparing the amount of labeled nucleic acid segment specifically bound to immobilized nucleic acid segments on the first array to the amount of labeled nucleic acid segments specifically bound to the same nucleic acid segment immobilized on the second array, and comparing the amount of labeled nucleic acid segments specifically bound to the calibration spot on the first and second arrays: and (d) normalizing the ratio of the amount of label associated with the nucleic acid segments in the first and second arrays by adjusting the ratio by a figure representing the difference between an expected ratio of label associated with the calibration spot on the first and second arrays and a detected ratio of label associated with the calibration spot on the first and second arrays, thereby determining the relative amount of a nucleic acid sequence complementary to a same nucleic acid segment present in the first sample compared to that present in the second sample.

2. The method of claim 1, wherein the first substrate surface and the second substrate surface comprise one surface and the first array and the second array are separated by a hydrophobic barrier such that a first sample can be applied to the first array at the same time a second sample is applied to the second array without the two samples mixing together.

3. The method of claim 1, wherein the first array and the second array are in separated wells of a multi-well plate.

4. The method of claim 3, wherein the multi-well plate is a multi-titer well plate and each well comprises one array.

5. The method of claim 1, wherein the nucleic acid comprises a nucleic acid analog or a nucleic acid mimetic thereof.

6. The method of claim 1, wherein the nucleic acid comprises a genomic nucleic acid.

7. The method of claim 6, wherein the genomic nucleic acid is a nucleic acid segment that comprises a gene.

8. The method of claim 6, wherein the genomic nucleic acid comprises a substantially complete chromosome or a known subset of a chromosome.

9. The method of claim 8, wherein the genomic nucleic acid comprises a substantially complete genome or a known subset of a genome.

10. The method of claim 6, wherein the genomic nucleic acid is derived from a genome of a normal cell.

11. The method of claim 6, wherein the genomic nucleic acid is derived from a genome of a mammalian cell.

12. The method of claim 11, wherein the mammalian cell is a human cell.

13. The method of claim 1, wherein the labeled nucleic acid segments comprise sequences complementary to a subset of transcripts expressed by a cell.

14. The method of claim 13, wherein the plurality of labeled nucleic acid segments comprise sequences complementary to a substantially complete sample of transcripts expressed by a cell.

15. The method of claim 1, wherein the plurality of labeled nucleic acid sequences comprise genomic sequences.

16. The method of claim 15, wherein the plurality of labeled nucleic acid sequences comprise a substantially complete chromosome or a known subset of a chromosome.

17. The method of claim 16, wherein the plurality of labeled nucleic acid sequences comprise a substantially complete genome or a known subset of a genome.

18. The method of claim 1, wherein the nucleic acid segments immobilized on the first and second arrays comprise nucleic acids comprising a substantially complete genome or a known subset of a genome and the labeled nucleic acid segments from each sample comprise a plurality of labeled nucleic acid sequences comprising a substantially complete genome or a known subset of a genome, thereby performing a comparative genomic hybridization.

19. The method of claim 1, wherein the nucleic acid from the first sample is derived from a cell with a normal genotype and the nucleic acid from the second sample is derived from a cell with an abnormal genotype.

20. The method of claim 1, wherein the nucleic acid from the first sample is derived from a cell with a normal phenotype and the nucleic acid from the second sample is derived from a cell with an abnormal phenotype.

21. The method of claim 20, wherein the abnormal phenotype comprises a disease phenotype.

22. The method of claim 20, wherein the abnormal phenotype comprises a neoplastic or hyperplastic phenotype.

23. The method of claim 22, wherein neoplastic phenotype is selected from the group consisting of breast cancer, skin cancer and bone cancer.

24. The method of claim 1, wherein the nucleic acid from the first sample is derived from an unstimulated cell and the nucleic acid from the second sample is derived from the unstimulated cell after stimulation.

25. The method of claim 1, wherein the nucleic acid from the first sample is derived from an undifferentiated cell and the nucleic acid from the second sample is derived from the undifferentiated cell after stimulation.

26. The method of claim 1, wherein the nucleic acid from the first sample is derived from a normal cell and the nucleic acid from the second sample is derived from the normal cell after an injury.

27. The method of claim 1, wherein the nucleic acid from the first sample is derived from a normal cell and the nucleic acid from the second sample is derived from the normal cell after an environmental stress.

28. The method of claim 27, wherein the environmental stress comprises a high or a low or a change in temperature.

29. The method of claim 27, wherein the environmental stress comprises an exposure to a chemical.

30. The method of claim 29, wherein the chemical is a carcinogen.

31. The method of claim 29, wherein the chemical is a drug or a medicine.

32. The method of claim 1, wherein the sample nucleic acid comprises a DNA.

33. The method of claim 1, wherein the sample nucleic acid comprises a cDNA or an RNA.

34. The method of claim 33, wherein the RNA comprises mRNA.

35. The method of claim 1, wherein the sample nucleic acid comprises oligonucleotides.

36. The method of claim 1, wherein the sample nucleic acid comprises expressed sequence tags (EST).

37. The method of claim 7, wherein the nucleic acid segment immobilized on the first and second arrays comprises genomic nucleic acid cloned in a construct comprising an artificial chromosome.

38. The method of claim 37, wherein the artificial chromosome comprises a bacterial artificial chromosome (BAC).

39. The method of claim 37, wherein the artificial chromosome is selected from the group consisting of a human artificial chromosome (HAC) a yeast artificial chromosome (YAC), a transformation-competent artificial chromosome (TAC) and a bacteriophage P1-derived artificial chromosome (PAC).

40. The method of claim 7, wherein the nucleic acid segment immobilized on the first and second arrays is cloned in a construct comprising a vector selected from the group consisting of a cosmid vector, a plasmid vector and a viral vector.

41. The method of claim 7, wherein the nucleic acid segment immobilized on the first and second arrays is between about 50 kilobases to about 500 kilobases in length, between about 100 kilobases to about 400 kilobases in length, or, is about 300 kilobases in length.

42. The method of claim 1, wherein a labeled nucleic acid is derived from a body fluid sample, a cell sample or a tissue sample.

43. The method of claim 1, wherein a labeled nucleic acid is derived from a cancer cell or a tumor cell sample.

44. The method of claim 1, wherein a labeled nucleic acid is derived from a biopsy sample.

45. The method of claim 1, wherein a labeled nucleic acid is derived from a blood sample.

46. The method of claim 7, further comprising a washing step, wherein sample nucleic acids not specifically hybridized to the nucleic acid segment immobilized on the first and second arrays are removed before the identifying step.

47. The method of claim 46, wherein the washing step comprises use of a solution comprising a salt concentration of about 0.02 molar at pH 7 at a temperature of at least about 50° C.

48. The method of claim 46, wherein the washing step comprises use of a solution comprising a salt concentration of about 0.15 M at a temperature of at least about 72° C. for about 15 minutes.

49. The method of claim 46, wherein the washing step comprises use of a solution comprising a salt concentration of about 0.2×SSC at a temperature of at least about 50° C. for at least about 15 minutes.

50. The method of claim 1, wherein the first sample nucleic acid and the second sample nucleic acid comprise the same label.

51. The method of claim 1, wherein the first sample nucleic acid and the second sample nucleic acid comprise different labels.

52. The method of claim 1, wherein the sample nucleic acids are labeled with a fluorochrome.

53. The method of claim 52, wherein the label comprises a Cy3™ or a Cy5™ or an equivalent.

54. The method of claim 1, wherein the sample nucleic acids are labeled with a bioluminescent or a chemiluminescent label.

55. The method of claim 1, further comprising a third array comprising a plurality of nucleic acids and at least one calibration spot, wherein each nucleic acids is immobilized to a discrete and known spot on a third substrate surface to form the third array of nucleic acids, and the nucleic acids immobilized on the third array comprise substantially the same plurality of nucleic acids and nucleic acid sequence markers arrayed as in the first and second arrays, and a third sample comprising a plurality of nucleic acids comprising a detectable label, the method further comprising contacting the third sample with the third array under the same conditions, thereby allowing the labeled nucleic acids to specifically bind to a nucleic acid immobilized on the third array; identifying which spots on the first, second and third substrate surfaces are specifically bound to a labeled sample nucleic acid and measuring the amount of label on each spot and on the calibration spot on the third array; and, comparing the amount of labeled nucleic acids bound by specific binding to the same nucleic acid immobilized on the first array, the second array and the third array and normalizing the ratio of the amount of label associated with the nucleic acid in the first, second and third arrays by adjusting the ratio by a figure representing the difference between an expected ratio of label associated with a calibration spot on the first, second and third ax-rays and a detected ratio of label associated with a calibration spot on the first, second and third arrays, thereby determining the relative amount of a nucleic acid in the first, second and third samples.

56. The method of claim 55, wherein the first, second and third substrate surfaces comprise one surface and the first, second and third arrays are separated by a hydrophobic barrier such that the samples can be applied to the arrays at the same time without the three samples mixing together.

57. The method of claim 55, wherein the first, second and third array are in separated wells of a multi-well plate.

58. The method of claim 57, wherein the multi-well plate is a multi-titer well plate and each well comprises one array.

59. The method of claim 1, further comprising the step of blocking the hybridization capacity of repetitive nucleic acid sequences in the immobilized nucleic acid.

60. The method of claim 1, further comprising the step of blocking the hybridization capacity of repetitive nucleic acid sequences in the sample nucleic acid sequences by mixing the sample nucleic acid sequences with unlabeled repetitive nucleic acid sequences.

61. The method of claim 60, wherein the sample nucleic acid sequences are first mixed with unlabeled repetitive nucleic acid sequences before the step comprising contacting with the nucleic acid segments immobilized on the first and second arrays.

62. The method of claim 60 or claim 61, wherein the repetitive nucleic acid sequences comprise Cot-1 DNA or equivalent.

63. The method of claim 60 or claim 61, wherein the repetitive nucleic acid sequences comprise SST sequences or salmon sperm DNA or equivalents.

64. An array-based method for performing comparative genomic hybridization, the method comprising:
(a) contacting a first sample and a second sample with a first array and a second array respectively, each array comprising a plurality of genomic nucleic acid segments, wherein each nucleic acid segment is immobilized to a discrete and known spot on a first substrate surface to form a first array of genomic nucleic acid segments wherein each said spot comprises a nucleic acid sequence that is a marker for each said spot on the array providing a plurality of markers on the array and the plurality of genomic nucleic acid segments comprise a substantially complete genome or a known subset of a genome and each array further comprising at least one calibration spot comprising a mixture of the same plurality of nucleic acid sequence markers present in all of the other spots of the, each sample comprising a plurality of genomic nucleic acid segments comprising a detectable label; wherein the contacting is performed under conditions wherein the labeled nucleic acid segments specifically bind to a nucleic acid segment immobilized on the first array;

(b) identifying which spots on the first and the second arrays are specifically hybridized to a labeled nucleic acid segment and measuring an amount of label on each spot; and (c) comparing the amount of labeled nucleic acid sequence bound by specific hybridization to a nucleic acid segment in the first array to the amount of labeled nucleic acid sequence bound by specific hybridization to a nucleic acid segment in the second array, and comparing an amount of a labeled nucleic acid sequence bound by specific hybridization to the calibration spots on the first array and the calibration spots on the second array;

(d) normalizing the ratio of the amount of label associated with a nucleic acid segment to each spot on the first and second arrays by a figure representing the difference between the amount of label bound to the calibration spot on the first array and the calibration spot on the second array, thereby determining the relative amount of a nucleic acid sequence complementary to the nucleic acid segment in the first sample compared to the second sample and performing a comparative genomic hybridization.

65. An array-based method of determining one or more variations in copy numbers of nucleic acid molecules in a first sample relative to copy numbers of substantially identical nucleic acid molecules in at least a second sample, the method comprising the steps of:

(a) contacting a first sample and at least a second sample with respectively a first array and at least a second array, each array comprising a plurality of immobilized nucleic acid molecules, wherein the nucleic acid molecules are immobilized to discrete and known spots on a substrate surface to form at least two arrays of nucleic acid molecules, wherein each said spot comprises a nucleic acid sequence that is a marker for each said spot on the array providing a plurality of markers on the array and the second array comprises substantially the same plurality of nucleic acid molecules immobilized in the first array, each array further comprising at least one calibration spot comprising a mixture of the same plurality of nucleic acid sequence markers present in all of the other spots of the array wherein at least two samples are labeled, and the two samples comprise the same label or nucleic acid molecules in the first sample comprise a different label than nucleic acid molecules in the second label, wherein the contacting is performed under conditions wherein the labeled sample nucleic acid molecules specifically bind to the immobilized nucleic acid molecules;

(b) detecting an amount of label associated with each spot and comparing the amount of label associated with an immobilized nucleic acid molecule in the first array to the amount of label associated with the same immobilized nucleic acid molecule in the second array and detecting an amount of label associated with the calibration spots on the first array and on the second array; and (c) normalizing the amount of label bound to each spot on the first and second arrays by adjusting the ratio by a figure representing the difference between an expected ratio of calibration molecules and a detected ratio of calibration molecules on the first and second arrays, thereby determining the one or more variations in copy numbers of immobilized nucleic acid molecule in the first sample relative to the second sample.

66. The method of claim 65, further comprising determining the ratio of the amount of label associated with the immobilized nucleic acid molecule in the first and the second array, thereby determining a ratio of signal intensity.

67. The method of claim 65, further comprising determining the amount of a calibration molecule, wherein a known amount of a calibration molecule is spotted on the calibration spots on each array.

68. The method of claim 67, wherein a known amount of a calibration molecule-binding composition is mixed with the first and the second samples.

69. The method of claim 65, comprising determining the average copy number of a calibration sequence, wherein a known amount of a calibration sequence is spotted on each array, and a known amount of the calibration sequence is mixed with the first and the second samples, and the calibration sequence is derived from a different source compared to that from which the sample nucleic acids were derived.

70. The method of claim 69, wherein the calibration sequence is derived from an organism different from which the sample nucleic acids were derived.

71. The method of claim 67, wherein the calibration molecule is spotted in titrated concentrations on each of the arrays.

72. The method of claim 67, further comprising determining whether the expected ratio of the known amount of calibration molecule is detected on the two arrays.

73. The method of claim 67, further comprising normalizing the ratio of the amount of label associated with a nucleic acid molecule in the first and second arrays by adjusting the ratio by a figure representing the difference between an expected ratio of calibration molecules and a detected ratio of calibration molecules on the two arrays.

* * * * *